United States Patent
Chen et al.

(10) Patent No.: US 10,745,370 B2
(45) Date of Patent: Aug. 18, 2020

(54) FARNESYL TRANSFERASE INHIBITORS AND USES THEREOF

(71) Applicant: Yu-Jen Chen, Taipei (TW)

(72) Inventors: Yu-Jen Chen, Taipei (TW); Lie-Chwen Lin, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 0 days.

(21) Appl. No.: 16/087,103

(22) PCT Filed: Mar. 20, 2017

(86) PCT No.: PCT/CN2017/077321
§ 371 (c)(1),
(2) Date: Sep. 21, 2018

(87) PCT Pub. No.: WO2017/162122
PCT Pub. Date: Sep. 28, 2017

(65) Prior Publication Data
US 2019/0084956 A1 Mar. 21, 2019

Related U.S. Application Data

(60) Provisional application No. 62/312,085, filed on Mar. 23, 2016.

(51) Int. Cl.
C07D 311/22 (2006.01)
A61P 37/06 (2006.01)
A61P 25/28 (2006.01)
A61P 35/00 (2006.01)

(52) U.S. Cl.
CPC ............ *C07D 311/22* (2013.01); *A61P 25/28* (2018.01); *A61P 35/00* (2018.01); *A61P 37/06* (2018.01)

(58) Field of Classification Search
CPC .............................. C07D 311/22; A61P 37/06
See application file for complete search history.

(56) References Cited

PUBLICATIONS

Papke et al (Science, 2017; 355:1158-1163) (Year: 2017).*
Appels et al (The Oncologist, 2005; 10:565-578) (Year: 2005).*
Wang et al (Med Chem Commun, 2017;8:841-854) (Year: 2017).*

* cited by examiner

*Primary Examiner* — Marcos L Sznaidman
*Assistant Examiner* — Rayna Rodriguez

(57) ABSTRACT

Disclosed herein are novel compounds and uses thereof. The present compounds may suppress the activity of farnesyl transferase and thus, may act as modulators of immune cells; therefor, they are useful for the development of a medicament for treating diseases that are associated with or caused by excessive levels of farnesyl transferase or immune response. Also disclosed herein are pharmaceutical compositions containing the present compounds.

3 Claims, 13 Drawing Sheets

FARNESYL TRANSFERASE INHIBITORS AND USES THEREOF

CROSS-REFERENCE TO RELATED APPLICATIONS

This application claims priority to U.S. Application No. 62/312,085, filed Mar. 23, 2016. The content of the above applications are incorporated by reference in its entirety

BACKGROUND OF THE INVENTION

1. Field of the Invention

The present disclosure relates to novel compounds and uses thereof. More particularly, the present disclosure relates to novel compounds with inhibitory effect on farnesyl transferase and immune cells, and their uses as medicaments for the treatment of tumor, neurodegenerative disease, premature aging disease, infectious disease, or immune disease.

2. Description of Related Art

Farnesyl transferase is one of the three enzymes in the prenyltransferase group. Structurally, it consists of two subunits: a 48 kDa alpha ($\alpha$) subunit and a 46 kDa beta ($\beta$) subunit. Both subunits are primarily composed of $\alpha$ helices. The $\alpha$ subunit is made of a double layer of paired $\alpha$ helices stacked in parallel, which wraps partly around the $\beta$ subunit like a blanket. The $\alpha$ helices of the $\beta$ subunit form a barrel. The active site is formed by the center of the $\beta$ subunit flanked by part of the $\alpha$ subunit.

Farnesyl transferase post-translationally-modifies proteins by adding an isoprenoid lipid called a farnesyl group to the —SH of the cysteine near the end of target proteins to form a thioether linkage. This process, called farnesylation, causes farnesylated proteins to become membrane-associated for the hydrophobic nature of the farnesyl group. Most farnesylated proteins are involved in cellular signaling pathways; one of the best-known farnesylated proteins is the Ras superfamily. It is known that Ras proteins promote cell proliferation and inhibit cell apoptosis via the mitogen-activated protein kinase (MAPK) and phosphatidylinositol 3 kinase (PI3K)/Akt signaling pathway. Further, the proteins are also involved in regulating various cellular processes, such as transcription, translation, cytoskeleton actin dynamics, adhesion, transformation, survival, migration, and immune response through activating the different effector proteins, including protein kinase C (PLCε), Ras and Rab interactor 1 (Rin1), Ral guanine nucleotide dissociation stimulator (RalGDS), and Tiam1, in which Tiam1 would further activate Rac, RhoB, NF-κB, and c-Jun N-terminal kinase (JNK).

The Ras proteins have to be farnesylated by farnesyl transferase to become functionally active before they may modulate downstream cellular processes. It has been reported that overexpression of farnesyl transferase may cause various types of diseases or pathological symptoms associated with abnormal cell growth, neurodegeneration, premature senescence, or abnormal immune response.

In view of the foregoing, there exists a need in the related art a farnesyl transferase inhibitor that suppresses the activity of farnesyl transferase, and accordingly may be useful as a lead compound for the development of a medicament for treating diseases and/or disorders associated with the activation of farnesyl transferase.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, disclosure herein features novel compounds, which may efficiently inhibit the activity of farnesyl transferase. Based on the inhibitory efficacy, the present disclosure also provides pharmaceutical compositions comprising the novel compounds, and the uses thereof.

Accordingly, the first aspect of the present disclosure pertains to a compound having a structure of formula (1):

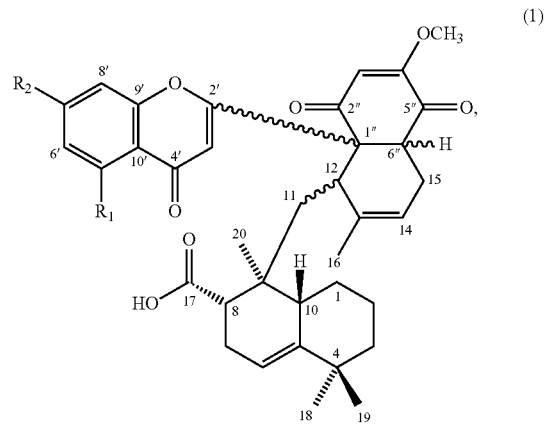

and its pharmaceutically acceptable salt, solvate, or stereoisomer, wherein $R_1$ is hydrogen or hydroxyl, and $R_2$ is hydroxyl or methoxy.

In some embodiments, the compound of formula (1) can be a compound of formula (1a), or its pharmaceutically acceptable salt, solvate, or stereoisomer:

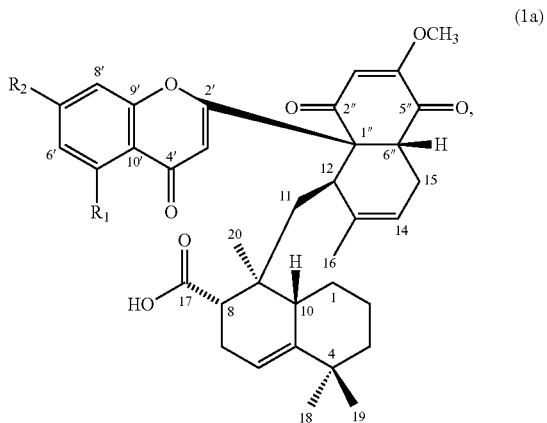

wherein $R_1$ is H or hydroxyl, and $R_2$ is hydroxyl or methoxy.

In others embodiments, the compound of formula (1) can be a compound of formula (1b), or its pharmaceutically acceptable salt, solvate, or stereoisomer:

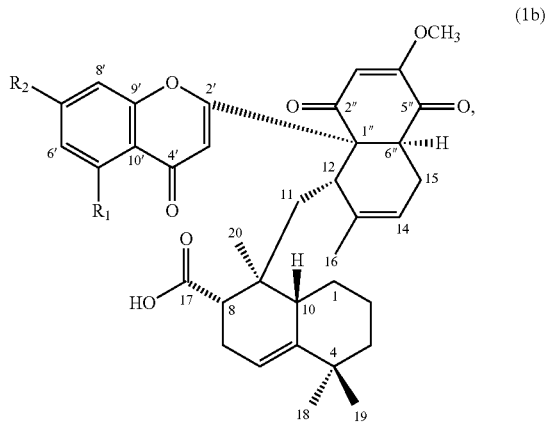

(1b)

wherein $R_1$ is H or hydroxyl, and $R_2$ is hydroxyl or methoxy.

The second aspect of the present disclosure relates to pharmaceutical compositions for treating a disease or a disorder associated with the activation of farnesyl transferase. The pharmaceutical composition comprises an effective amount of the compound described above, its pharmaceutically acceptable salt, solvate, or stereoisomer; and a pharmaceutically acceptable carrier.

According to some embodiments of the present disclosure, the disease or disorder associated with the activation of farnesyl transferase can be tumor, neurodegenerative disease, premature aging disease, infectious disease, or immune disease.

The third aspect of the present invention is directed to a method for treating a subject having or suspected of having a disease or a disorder associated with the activation of farnesyl transferase. The method comprises the step of, administering to the subject a therapeutically effective amount of one or more compounds described above, the pharmaceutically acceptable salt, solvate, or derivate thereof, or the pharmaceutical compositions described herein.

In embodiments of the present disclosure, the disease or disorder associated with the activation of farnesyl transferase is tumor, neurodegenerative disease, premature aging disease, infectious disease, or immune disease.

According to one embodiment, the tumor can be melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cholangiocarcinoma, uterine cancer, cervical cancer, ovarian cancer, prostate cancer, or head and neck squamous cell carcinoma.

According to another embodiment, the neurodegenerative disease is selected from the group consisting of Alzheimer's disease, Parkinson's disease, Huntington's disease, and Amyotrophic lateral sclerosis.

According to still another embodiment, the premature aging disease can be progeria.

According to further another embodiment, the infectious disease may be caused by parasite, virus, or bacteria.

In certain embodiments, the immune disease is any of autoimmune disease, transplantation-related disease, allergic disease, inflammatory disease, septicemia or shock.

In one specific embodiment, the subject being treated by the present method is a human, and the therapeutically effective amount of the compound is about 0.08-10.0 mg/Kg. Preferably, the therapeutically effective amount of the compound is about 1 mg/Kg.

The fourth aspect of the present disclosure is directed to a method for suppressing the growth, differentiation, or function of an immune cell in vitro. The method comprises the step of, incubating an effective amount of one or more compounds described above, the pharmaceutically acceptable salt, solvate, or derivate thereof, or the pharmaceutical compositions described herein, with the immune cell.

According to some embodiments of the present disclosure, the immune cell is an antigen-presenting cell. In one specific embodiment, the antigen-presenting cell is dendritic cell. In another specific embodiment, the antigen-presenting cell is macrophage.

According to other embodiments of the present disclosure, the effective amount of the compound is at least 1 μM; preferably, the effective amount of the compound is about 1-100 μM; most preferably, the effective amount of the compound is about 2-50 μM.

Many of the attendant features and advantages of the present disclosure will become better understood with reference to the following detail description.

BRIEF DESCRIPTION OF THE DRAWINGS

The present description will be better understood from the following detailed description read in light of the accompanying drawings, where.

Figure 1:
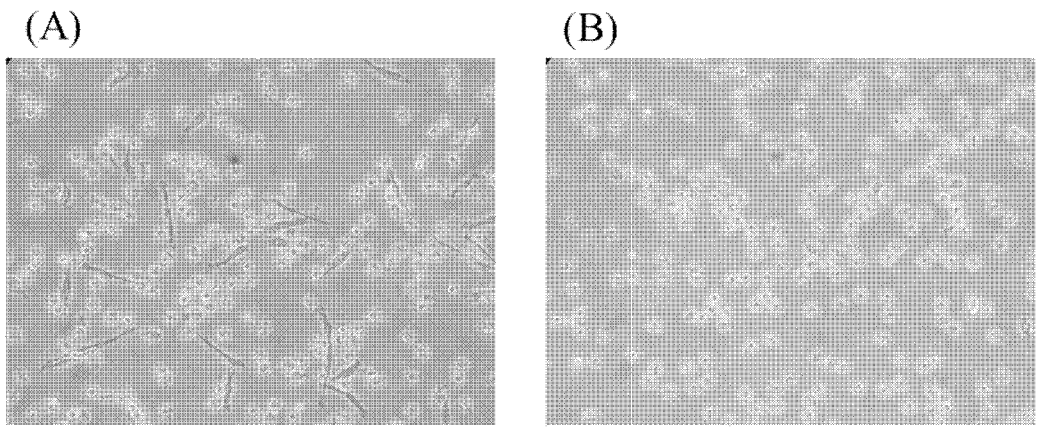
FIG. 1 are photographs illustrating the morphology of macrophages treated with (A) Mib-8 or Mib-10, (B) Mib-5, Mib-6, or Mib-7, or (c) specified treatment according to one example of the present disclosure.
Figure 1:
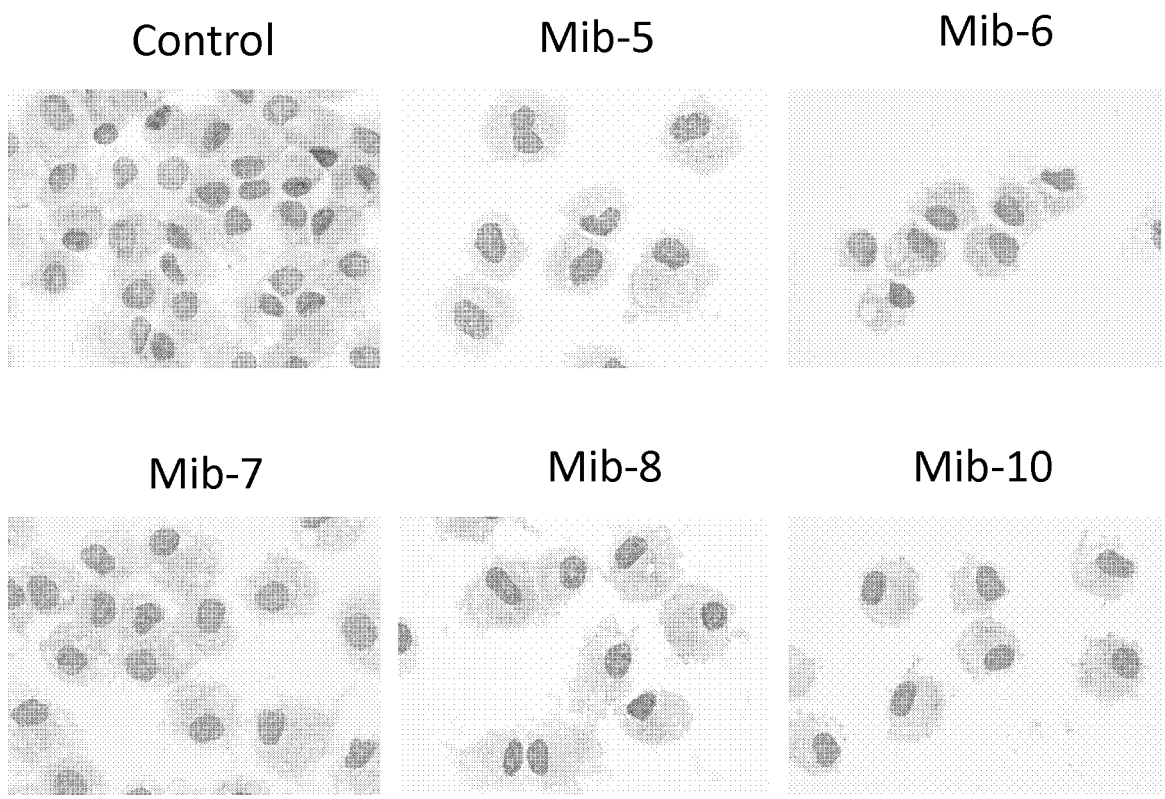

In accordance with common practice, the various described features/elements are not drawn to scale but instead are drawn to best illustrate specific features/elements relevant to the present invention.

DETAILED DESCRIPTION OF PREFERRED EMBODIMENTS

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

The terms "a", "an", and "the" as used herein are defined to mean "one or more" and include plural referents unless the context clearly dictates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, a "pharmaceutically acceptable carrier" is one that is suitable for use with the subjects without undue adverse side effects (such as toxicity, irritation, and allergic response) commensurate with a reasonable benefit/risk ratio. Also, each carrier must be "acceptable" in the sense of being compatible with the other ingredients of the pharmaceutical composition. The carrier can be in the form of solid, semi-solid, liquid diluent, cream or capsule.

As used herein, the term "treating" encompasses partially or completely preventing, ameliorating, mitigating and/or managing a symptom, a secondary disorder or a condition associated with farnesyl transferase. The term "treating" as used herein refers to application or administration of one or more compounds of the present disclosure, or the composition comprising the same in accordance with the present disclosure, to a subject, who has a symptom, a secondary disorder, or a condition associated with farnesyl transferase, with the purpose to partially or completely alleviate, ameliorate, relieve, delay onset of, inhibit progression of, reduce severity of, and/or reduce incidence of one or more symptoms, secondary disorders or features of farnesyl transferase. Symptoms, secondary disorders, and/or conditions associated with farnesyl transferase include, but are not limited to, tumor, neurodegenerative disease, premature aging disease, infectious disease, and immune disease. Treatment may be administered to a subject who exhibits only early signs of such symptoms, disorder, and/or condition for the purpose of decreasing the risk of developing the symptoms, secondary disorders, and/or conditions associated with farnesyl transferase. Treatment is generally "effective" if one or more symptoms or clinical markers are reduced as that term is defined herein. Alternatively, a treatment is "effective" if the progression of a symptom, disorder or condition is reduced or halted.

The term "therapeutically effective amount" as used herein refers to the quantity of a component (such as the compound of the present invention) which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. A therapeutically effective amount is also one in which any toxic or detrimental effects of the component or composition are outweighed by the therapeutically beneficial effects. Effective amount may be expressed, for example, in grams, milligrams or micrograms or as milligrams per kilogram of body weight (mg/kg). Alternatively, the effective amount can be expressed in the concentration of the active component in the pharmaceutical composition, such as molar concentration, mass concentration, volume concentration, molality, mole fraction, mass fraction and mixing ratio. Persons having ordinary skills could calculate the human equivalent dose (HED) for the medicament (such as the compounds of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with the compounds of the present disclosure, the composition comprising the same and/or methods of the present invention. The term "subject" is intended to refer to both the male and female gender unless one gender is specifically indicated, and may be any age, e.g., a child or adult.

The subject invention is directed to a compound of formula (1), a pharmaceutical composition comprising the same, and uses thereof:

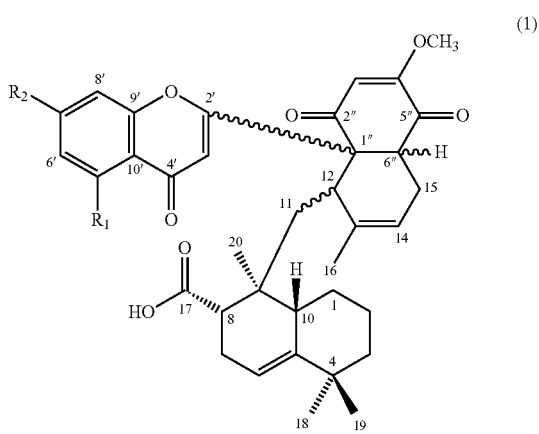

wherein, $R_1$ is hydrogen or hydroxyl; and $R_2$ is hydroxyl or methoxy.

Additionally, salts, and solvates of the compound of formula (1) are also included in the present disclosure and can be used in the composition and/or methods disclosed herein. Each compounds of the present invention contain one or more stereocenters, thus can exist as racemic mixtures of enantiomers or mixtures of diastereomers. This invention thus encompasses stereomerically pure forms of such compounds, as well as mixtures of those forms. Stereoisomers may be asymmetrically synthesized or resolved using standard techniques such as crystallization, chromatography, and the use of a resolving agent. One preferred way of separating enantiomers from a racemic mixture is by use of preparative high performance liquid chromatography (HPLC). Alternatively, the racemic may be separated into its enantiomers by reacting with an optically active form of a resolving agent in the presence of a solvent. Depending on the optical form of the resolving agent, one of the two enantiomers is separated out as an insoluble salt with high yield and high optical purity, while the opposite enantiomer remains in the solution. The present invention thus further encompasses stereoisomeric mixtures of compounds disclosed herein. It also encompasses configurational isomers of compounds disclosed herein (e.g., cis and trans isomers, whether or not involving double bonds), either in admixture or in pure or substantially pure form. The present disclosure thus further includes all possible stereoisomers and geometric isomers of the compound of formula (1). The present invention includes both racemic compounds and optically active isomers. Additionally, in situations where tautomers of the compound of formula (1) are possible, the present disclosure is intended to include all tautomeric forms of the compounds.

Compounds of the present disclosure can also exist as salts. Pharmaceutically acceptable salts of the present disclosure often are preferred in the methods of the invention. Salts of compound of formula (1) can be prepared during the final isolation and purification of the compounds or separately by reacting the compound with an acid having a suitable cation. The pharmaceutically acceptable salts of compound of formula (1) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Non-limiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In light of the foregoing, any reference to compound of formula (1) appeared herein is intended to include compound of formula (1) as well as pharmaceutically acceptable salts, or solvates thereof.

As described in introduction, farnesyl transferase participates in the regulation of different cellular processes via Ras signaling pathway; accordingly, the overexpression of farnesyl transferase may causes diseases, such as tumor, neurodegeneration, premature senescence, and abnormal immune response. According to the embodiments of the present disclosure, the compound of formula (1) may inhibit the activity of farnesyl transferase, and thus, are potential lead compounds for manufacturing a medicament for treating a disease and/or a disorder associated with the activation of farnesyl transferase.

Further, accordingly to some embodiments of the present disclosure, the present compound of formula (1) may suppress the growth, differentiation, or function of an immune cell. In one embodiment, the immune cell is a dendritic cell. In another embodiment, the immune cell is a macrophage. It is known that both the dendritic cell and the macrophage are antigen-presenting cells, which present the antigen to T cells so as to elicit the immune response. Accordingly, in addition to the disease associated with farnesyl transferase overexpression as described above, the compound of formula (1) is also useful in manufacturing a medicament for treating the disease associated with abnormal and/or inappropriate immune response.

Specifically, examples of disease treatable by the compound of formula (1) include, but are not limited to, tumor, neurodegenerative disease, premature aging disease, infectious disease, and immune disease. More specifically, the tumor can be any of melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cholangiocarcinoma, uterine cancer, cervical cancer, ovarian cancer, prostate cancer, or head and neck squamous cell carcinoma. The neurodegenerative disease is selected from the group consisting of Alzheimer's disease, Parkinson's disease, Huntington's disease, and Amyotrophic lateral sclerosis. The premature aging disease can be progeria. The infectious disease may be parasite infection, viral infection, or bacterial infection. The immune disease is any of autoimmune disease, transplantation-related disease, allergic disease, inflammatory disease, septicemia, shock, or other diseases resulting from abnormal immune responses or excessive immune responses.

In certain embodiments, the compound of formula (1) is a compound of formula (1a):

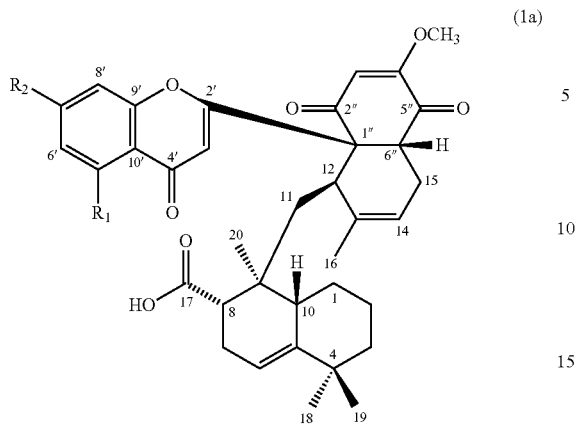

(1a)

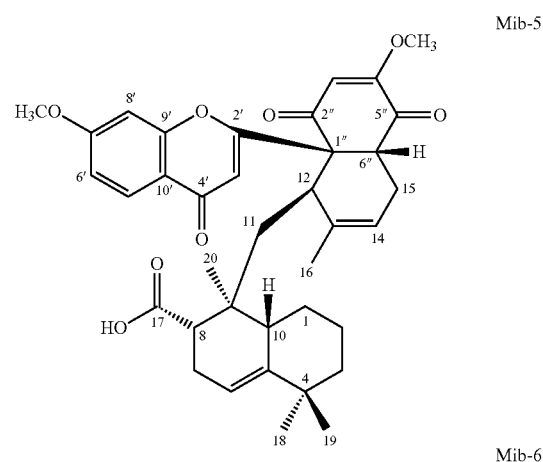

Mib-5

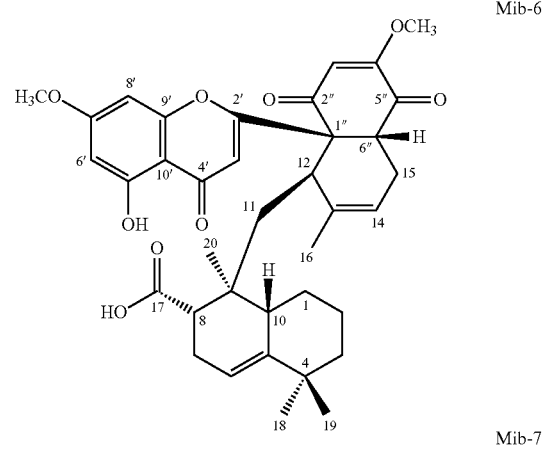

Mib-6 wherein, $R_1$ is hydrogen or hydroxyl; and $R_2$ is hydroxyl or methoxy.

According to one embodiment, the present disclosure provides a compound Mib-5 that has the structure of formula (1a), in which the $R_1$ is hydrogen, and $R_2$ is methoxy. According to another embodiment, the present disclosure provides a compound Mib-6 that has the structure of formula (1a), in which the $R_1$ is hydroxyl, and $R_2$ is methoxy. According to still another embodiment, the present disclosure provides compound Mib-7 that has the structure of formula (1a), in which both the $R_1$ and $R_2$ are hydroxyl. According to further embodiment, the present disclosure provides a compound Mib-9 that has the structure of formula (1a), in which $R_1$ is hydrogen, and $R_2$ is hydroxyl.

In other embodiments, the compound of formula (1) is a compound of formula (1b):

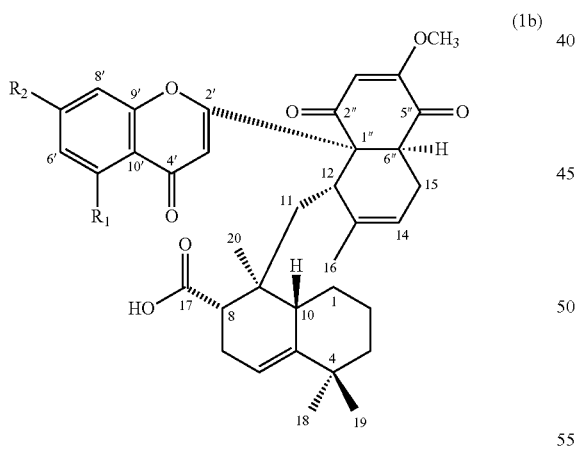

(1b)

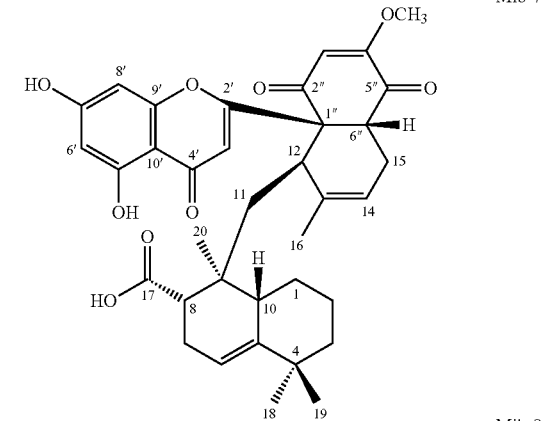

Mib-7

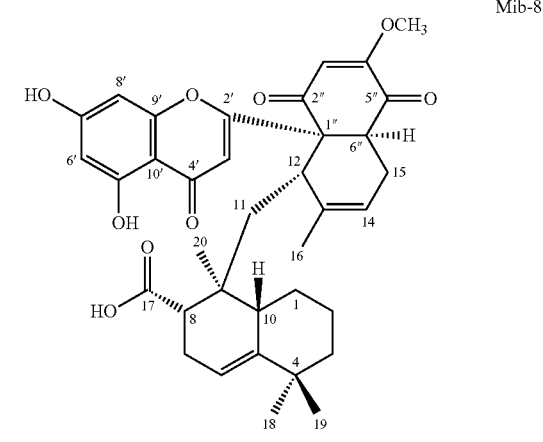

Mib-8 wherein, $R_1$ is hydrogen or hydroxyl; and $R_2$ is hydroxyl or methoxy.

According to one specific embodiment, the present disclosure provides a compound of formula (1b), in which both $R_1$ and $R_2$ are hydroxyl (i.e., Mib-8). According to another specific embodiment, the present disclosure provides a compound of formula (1b), in which the $R_1$ is hydrogen, and $R_2$ is hydroxyl (i.e., Mib-10).

The compound of formula (1) encompasses the following compounds:

-continued

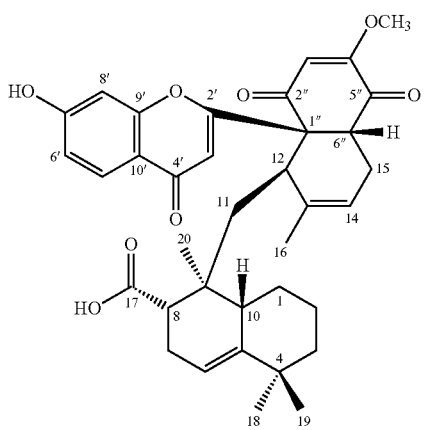

Mib-9

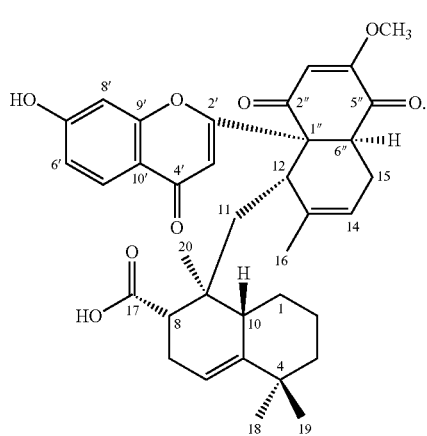

Mib-10

The compound of formula (1) may be prepared by any suitable method familiar to the skilled artisan. For example, the compound of formula (1) may be purified form the plant, *Mimosa diplotricha*, in accordance with steps described in working examples of the present disclosure.

The second aspect of the present disclosure pertains to a method for treating a subject having or suspected of having a disease or a disorder associated with the activation of farnesyl transferase. More specifically, the disease or disorder can be tumor, neurodegenerative disease, premature aging disease, infectious disease, or immune disease.

The method described herein relates to the use of a compound of formula (1), particularly the use of the compound of formula (1a) or (1b), in the treatment of diseases associated with the activation of farnesyl transferase. The method of the present disclosure can be accomplished by administering to the subject a compound of formula (1) as the neat compound or as a pharmaceutical composition. Administration of a pharmaceutical composition, or neat compound of formula (1), can be performed during or after the onset of the disease or condition of interest. Typically, the pharmaceutical compositions are sterile, and contain no toxic, carcinogenic, or mutagenic compounds that would cause an adverse reaction when administered.

According to some embodiments of the present disclosure, the tumor that is treatable with the present method can be any of melanoma, leukemia, brain tumor, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, cholangiocarcinoma, uterine cancer, cervical cancer, ovarian cancer, prostate cancer, or head and neck squamous cell carcinoma. The neurodegenerative disease is selected from the group consisting of Alzheimer's disease, Parkinson's disease, Huntington's disease, and Amyotrophic lateral sclerosis. The premature aging disease can be progeria. The infectious disease may be parasite infection, viral infection, or bacterial infection. The immune disease is any of autoimmune disease, transplantation-related disease, allergic disease, inflammatory disease, septicemia, shock, or other diseases resulting from abnormal immune responses or excessive immune responses.

In some embodiments, the method comprises administering the subject a therapeutically effective amount of the compound of formula (1). In one specific embodiment, the method comprises administering the subject a therapeutically effective amount of the compound of formula (1a); while in another specific embodiment, the method comprises administering the subject a therapeutically effective amount of the compound of formula (1b).

According to one embodiment of the present disclosure, the subject is a mouse, and the therapeutically effective amount of the present compound (i.e., the compound of formula (1)) is about 1-100 mg/Kg; that is, the therapeutically effective amount can be 1, 2, 3, 4, 5, 6, 7, 8, 9, 10, 20, 30, 40, 50, 60, 70, 80, 90, or 100 mg/Kg. Preferably, the therapeutically effective amount is about 5-50 mg/Kg. In one working example, the therapeutically effective amount is 10 mg/Kg.

A skilled artisan could calculate the human equivalent dose (HED) for the present compound of the present compound (i.e., the compound of formula (1)), based on the doses determined from animal models. Accordingly, the therapeutically effective amount is about 0.08-10.0 mg/Kg for human; that is, the therapeutically effective amount can be 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, or 10.0 mg/Kg. In one preferred embodiment, the therapeutically effective amount is about 0.5-5.0 mg/Kg. More preferably, the therapeutically effective amount is about 1.0 mg/Kg.

The compounds of the present disclosure (e.g., the compound of formula (1)) may be formulated into pharmaceutical compositions by combining with appropriate pharmaceutically acceptable carriers or excipients, and may be formulated into solid, semi-solid, or liquid forms, such as tablets, capsules, powders, granules, ointments, solutions, suppositories, and injections. As such, administration of the active compound can be achieved in various ways, including oral, buccal, rectal, parental, intraperitoneal, and etc. administration. In pharmaceutical dosage forms, the active compound may be administered alone or in combination with other known pharmaceutically active agent to treat diseases and conditions wherein inhibition of HDAC and HMGR provides a benefit. One of skilled person in the art is familiar with the various dosage forms that are suitable for use in each route. It is to be noted that the most suitable route in any given case would depend on the nature or severity of the disease or condition being treated.

In some embodiments, the pharmaceutical compositions of this disclosure are solid dosage forms for oral administration. Such solid dosage forms may be capsules, sachets, tablets, pills, lozenges, powders or granules. In such forms, the active ingredient such as any of the compounds described above is mixed with at least one pharmaceutically acceptable excipient. Any of the described solid dosage forms may optionally contain coatings and shells, such as enteric coatings, and coatings for modifying the release rate of any of the ingredients. Examples of such coatings are well known in the art. In one example, the pharmaceutical compositions of this disclosure are tablets such as quick-release tablets. In still another example, the pharmaceutical compositions of this disclosure are formulated into sustained release forms. In another example, the pharmaceutical compositions of this disclosure are powders that are encapsulated in soft and hard gelatin capsules.

In some embodiments, the pharmaceutical compositions of the present disclosure are liquid dosage forms for oral administration. The liquid formulation may further include a buffering agent to maintain a desired pH. The liquid dosage formulations may also be filled into soft gelatin capsules. For example, the liquid may include a solution, suspension, emulsion, micro-emulsion, precipitate or any desired liquid media carrying any of the compound as described above, or a pharmaceutically acceptable salt, solvate, or stereoisomer thereof, or a combination thereof. The liquid may be designed to improve the solubility of active compound as described above to form a drug-containing emulsion or disperse phase upon release.

In some embodiments, the pharmaceutical compositions of this disclosure are formulations suitable for parenteral administration, such as administration by injection, which includes, but is not limited to, subcutaneous, bolus injection, intramuscular, intraperitoneal and intravenous injection. The pharmaceutical compositions may be formulated as isotonic suspensions, solutions or emulsions in oily or aqueous vehicles, and may contain formulatory agents such as suspending, stabilizing or dispersing agents. Alternatively, the compositions may be provided in dry form such as powders, crystallines or freeze-dried solids with sterile pyrogen-free water or isotonic saline before use. They may be presented in sterile ampoules or vials.

In light of the inhibitory effect on the immune cell, the third aspect of the present disclosure is directed to a method for suppressing the growth, differentiation, or function of an immune cell in vitro. The method comprises the step of, incubating an effective amount of the compound of formula (1) or its pharmaceutical composition with the immune cell.

According to some embodiments of the present disclosure, the immune cell is an antigen-presenting cell, such as a dendritic cell, and a macrophage. In these embodiments, the effective amount is at least 1 µM. Preferably, the effective amount is about 1-100 µM, such as 1, 2, 3, 4, 5, 6, 7, 8, 9, 10, 15, 20, 25, 30, 35, 40, 45, 50, 55, 60, 65, 70, 75, 80, 85, 90, 95, or 100 µM. More preferably, the effective amount is about 2-50 µM. According to one specific embodiment, 10 µM of the compound of formula (1) is sufficient to inhibit the growth, differentiation, or function of the dendritic cell or the macrophage in vitro.

There are two main groups of macrophage: M1 macrophage (also known as classically activated macrophage) and M2 macrophage (also known as alternatively activated macrophage). M1 macrophage is activated by lipopolysaccharides (LPS) or interferon-γ (IFN-γ), and it secrets high levels of interleukin-12 (IL-12) and low levels of IL-10; accordingly, M1 macrophage usually would induce inflammatory response. By contrast, M2 macrophage is activated by IL-4, and produces anti-inflammatory cytokines, such as IL-10, and tumor growth factor-β (TGF-β); thus, M2 macrophage generally will promote anti-inflammatory response. According to one embodiment of the present disclosure, administering an effective amount of the present compound (i.e., the compound of formula (1)) or its pharmaceutical composition to a population of macrophages decreases the cell viability, and tilts the balance between the M1 and M2 populations of macrophages towards M2 population of macrophage via downregulating the expression of CD80 (a differentiating marker of M1 macrophage), and upregulating the expression of CD206 (a differentiating marker of M2 macrophage).

According to another embodiment of the present disclosure, administering an effective amount of the present compound (i.e., the compound of formula (1)) or its pharmaceutical composition to dendritic cell decreases the cell viability, and downregulates the expression of the differentiation marker (e.g., CD1a) and maturation marker (e.g., CD83).

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods
Cell Culture and Treatment

Mononuclear cells (MNCs) were separated from the peripheral blood of healthy donors obtained with written consent by use of Ficoll-Hypaque density centrifugation, followed by positive selection with magnetic anti-CD14 microbeads.

The isolated CD14$^+$ cells were cultivated in Minimum Essential Medium (MEM medium) supplemented with 10% fetal bovine serum (FBS), 100 ng/ml granulocyte-macrophage colony-stimulating factor (GM-CSF, Gentaur), and 50 ng/ml interleukin-4 (IL-4, R&D), and kept in an environment of 37° C. with 5% $CO_2$/95% air.

To evaluate the effects of the present compound on dendritic cells, the CD14$^+$ cells were respectively treated with 10 µM of test compound (i.e., Mib-5, Mib-6, Mib-7, Mib-8, Mib-9, and Mib-10) on day 1. Then, on day 3, the cultured medium in each well was replenished by adding half the volume of the cultured medium containing the same treatment as indicated above. Then, on day 6, a cytokine cocktail containing IL-1, IL-6, and tumor necrosis factor-α (TNF-α) was added to induce maturation. On day 7, the differentiated dendritic cells were collected and subjected to further assays, including viability assay, morphology observation, and cell marker staining.

As to the effects of the present compound on macrophages, the CD14$^+$ cells were cultivated and treated as indicated above except the addition of cytokine cocktail on day 6. The macrophages were collected on day 6 and subjected to further assays, including viability assay, trypan blue exclusion test, morphology observation, cell marker staining, and phagocytotic activity analysis.

Differentiation Analysis

M1 differentiation of freshly isolated CD14$^+$ cells was induced by the addition of lipopolysaccharide (LPS), while M2 differentiation of freshly isolated CD14$^+$ cells was induced by the addition of IL-4. Then, the present compounds (e.g., Mib-5, 6, 7, 8, 9, or 10) were added at the indicated dosages. 6 days later, the population of the differentiated macrophages were then determined by cell viability analysis.

Trypan Blue Exclusion Test

The dye exclusion test is used to determine the number of viable cells present in a cell suspension. It is based on the principle that live cells possess intact cell membranes that exclude certain dyes, such as trypan blue, eosin, or propidium, whereas dead cells do not. In this test, the cells were first treated with a test compound (i.e., Mib-5, 6, 7, 8, 9 or 10) for a certain period of time (e.g., 72 hours), then the cells were harvested and re-suspended in suitable buffer solution. The cell suspension was then mixed with trypan blue dye and then visually examined to determine whether cells had taken up or excluded the dye. A viable cell will have a clear cytoplasm, whereas a nonviable cell will have a blue cytoplasm. The concentration required to reduce viability by 50% ($IC_{50}$) after 72 hours was extrapolated from the dose-response curves by different concentrations of the test compound using a second-order polynomial regression model and analyzing with SigmaPlot Software (Systat Software Inc., San Jose, Calif.).

Morphology Analysis by Liu's Staining

Cells were transferred to a glass coverslide and covered with solution A (0.5 g of methylene blue and 1.7 g of Eosin yellow dissolved in 1,000 ml of ethanol). After 45 seconds, solution B (1.3 g of azure, 1.4 g of methylene blue, 23.38 g of $Na_2HPO_4$, 6.5 g of $KH_2PO_4$, dissolved in 1,000 ml of distilled water) was added in the proportion of 2 parts of B to 1 part of A. Mixed the solutions well by blowing the surface. The slide was left standing for 90 seconds and then washed off the staining solution rapidly by running water. The morphology of stained cells was then examined under microscope.

Cell Viability Test

The cell viability was measured by cell counting kit-8 (CCK-8, Sigma). The half maximal inhibitory concentrations ($IC_{50}$) of the test compounds on macrophages or dendritic cells were calculated.

Cell Marker Analysis and Staining

The expression of various types of cell markers, such as CD14, CD206, and CD80 expressed on the surface of macrophages, and CD1a, CD14, CD83, and HLA-DR expressed on the dendritic cells, were respectively detected by fluorescein isothiocyanate (FITC) and phycoerythrin (PE)-conjugated monoclonal antibodies in FACS caliber flowcytometer. Monoclonal antibodies used in this examples included anti-CD14 (IgG-FITC), anti-CD206 (IgG-FITC), anti-CD80-PE, anti-CD1a-PE, anti-CD83-PE and anti-human leukocyte antigen (HLA)-DR-PE. Results were analyzed by CellQuest software.

Phagocytosis Assay

The phagocytic activity of macrophages was measured by using flow cytometric analysis. The green fluorescent latex beads (carboxylate-modified beads with diameter 2 μm) were suspended in PBS solution and added into macrophage culture for 2 hours with vortexa at 37° C. The macrophages were subjected to flow cytometry for measurement of fluorescent intensity Inhibition of Farnesyl Transferase The assay was carried out in 384-well microplates with a final volume of 20 μl by the method modified from the previous report (Long et al., 2009). Briefly, 10 nM of rat PFTase (Jena Biosciences, Jena, Germany) was incubated with the tested compound or DMSO (1%) for 15 min, and then the mixture was added in a solution (50 mM Tris-HCl, pH 7.5, 5 mM $MgCl_2$, 5 mM DTT, 0.1 mM $ZnCl_2$, 0.2% octyl-β-D-glucopyranoside (Sigma, St. Louis, Mo.), 10 μM PFTase substrate dansyl-Gly-Cys-Val-Leu-Ser-OH, and 10 μM farnesyl pyrophosphate (Sigma, St. Louis, Mo.)) to initiate the reaction. The reaction was incubated at 37° C. for 30 min, and the fluorescence was detected by a M5 plate reader (Molecular Devices, CA, USA) at 340 nm excitation and 505 nm emission.

Animal Experiment

Six- to eight-week-old male C57BL/6($H-2^b$) and BALB/c($H-2^d$) mice were purchased from the Animal Resource Center of the National Science Council of Taiwan (Taipei, Taiwan). All animal experiments were approved by the animal ethics committee of Mackay Memorial Hospital. Surgery for skin transplantation was performed with standardized procedures. In brief, a 2×1 cm full-thickness skin graft was harvested from the C57BL/6 donor mouse. A graft bed on the BALB/c recipient was prepared. The skin graft was sutured to the recipient's graft bed. Rejection was defined as necrosis of more than 80% of the epidermal surface of the graft. The tested agents included vehicle (as control), Mib-5 (10 mg/kg/day), Mib-7 (10 mg/kg/day) and rapamycin (1.5 mg/kg/day as positive control). Treatments were administered intraperitoneally daily for consecutive 20 days until rejection was observed.

Example 1 Preparation and Characterization of the Compounds of Formula (1)

1.1 Preparation of the Compound of Formula (1)

The dried plant of *Mimosa diplotricha* (300 g) was extracted at room temperature with EtOAc (2 L) for overnight. The extract was concentrated at reduced pressure, the residue was then partitioned between MeOH and hexane, and further subjected to silica gel column chromatography using a gradient of $CH_2Cl_2$ and MeOH. The fractions were further analyzed by TLC, and each fractions of TLC was further purified by RP 18 chromatography to give Mib-5, Mib-6, Mib-7, Mib-8, Mib-9, and Mib-10. The structure of each Mib-5 to 10 was confirmed by NMR and MS spectra analysis.

1.2 Structure of the Present Compounds

In this example, the structures of compounds of formula (1a) and (1b) were analyzed by 1D, 2D NMR, UV, and HR MS spectral assays. The absolute configurations were determined by X-ray crystallization analysis and CD spectra. The absolute configurations of 8S, 9S, 10S, 12R, 1"S, and 6"R were found in compounds Mib-5, 6, 7, and 9; and 8S, 9S, 10S, 12S, 1"R, and 6"S in compounds Mib-8 and 10.

1.2.1 Mib-5

UV (MeOH) $\lambda_{max}$ (log ε) 281 (4.06) nm; IR (KBr) $v_{max}$ 3429, 1705, 1625, 1604, 1439, 1376, 1366, 1204, 1165, 1089 $cm^{-1}$; $[\alpha]^{26}_D$ −82.4° (c 0.38, MeOH); $^1$H NMR ($CDCl_3$, 600 MHz); $^{13}$C NMR ($CDCl_3$, 150 MHz) see Tables 1 and 2; ESIMS m/z 613 $[M-H]^-$; HRESIMS m/z 615.2970 $[M+H]^+$ (calcd for $C_{37}H_{43}O_8$, 615.2958); CD [nm (Δε (3.2 mg/50 ml MeOH): 307 (−0.3), 288 (+6.5), 273 (−0.5), 260 (+4.3), 241 (−6.1), 234 (−4.8), 211 (−8.4).

1.2.2 Mib-6

UV (MeOH) $\lambda_{max}$ (log ε) 255 (4.43) nm; IR (KBr) $v_{max}$ 3534, 3400, 1707, 1660, 1609, 1433, 1344, 1205, 1160, 1113, 1080 $cm^{-1}$; $[\alpha]^{26}_D$ −172.8° (c 0.415, $CHCl_3$); $^1$H NMR ($CDCl_3$, 600 MHz); $^{13}$C NMR ($CDCl_3$, 150 MHz) see Tables 1 and 2; ESIMS m/z 629 $[M-H]^-$; HRESIMS m/z 631.2914 $[M+H]^+$ (calcd for $C_{37}H_{43}O_9$, 631.2907); CD [nm (Δε (2.9 mg/50 ml MeOH): 356 (−1.0), 323 (+1.5), 294 (−5.1), 269 (+23.0), 249 (−19.6), 229 (−10.3), 214 (−17.7).

Mib-6 was further subjected to X-ray analysis, in which a suitable colorless crystal (0.20×0.15×0.05 $mm^3$), grown by slow evaporation of MeOH solution, was mounted on a Nonius CCD diffractometer equipped with Cu radiation (λ=1.54178 Å). Crystal data: $C_{37}H_{46}O_{11}$, Mr=666.74 g/mol, orthorhombic. Cell parameter: a=10.4620(11) Å, b=12.5584(8) Å, c=26.2046(19) Å, V=3442.9(5) $Å^3$, space group $P2_12_12_1$ (Z=4), $D_{calc}$=1.286 mg/$m^3$, F(000)=1424. A total of 7104 reflections were collected (4821 unique, $R_{int}$=0.0913) in the range 3.90°<θ<67.99°. The structure was solved using direct methods and refined by Full-matrix least-squares on $F^2$ values. The final indices were $R_1$=0.0799, $wR_2$=0.2036 with goodness-of-fit=1.069.

1.2.3 Mib-7

UV (MeOH) $\lambda_{max}$ (log ε) 255 (4.08) nm; IR (KBr) $\nu_{max}$ 3432, 1722, 1659, 1607, 1443, 1352, 1155, 1108 cm$^{-1}$; $[\alpha]^{26}_D$ −124.8° (c 0.52, MeOH); $^1$H NMR (CD$_3$OD, 600 MHz); $^{13}$C NMR (CD$_3$OD, 150 MHz) see Tables 1 and 2; ESIMS m/z 615 [M−H]$^-$; HRESIMS m/z 617.2745 [M+H]$^+$ (calcd for C$_{36}$H$_{41}$O$_9$, 617.2751); CD [nm (Δε (2.6 mg/50 ml MeOH): 357 (−0.5), 324 (+0.6), 295 (−2.6), 269 (+10.1), 248 (−8.9), 227 (−4.7), 206 (−12.4).

1.2.4 Mib-8

UV (MeOH) $\lambda_{max}$ (log ε) 256 (4.16) nm; IR (KBr) $\nu_{max}$ 3465, 1703, 1661, 1606, 1443, 1410, 1356, 1208, 1172, 1097, 1026 cm$^{-1}$; $[\alpha]^{26}_D$ +172.9° (c 0.45, MeOH); $^1$H NMR (CD$_3$OD, 600 MHz); $^{13}$C NMR (CD$_3$OD, 150 MHz) see Tables 1 and 2; ESIMS m/z 615 [M−H]$^-$; HRESIMS m/z 617.2754 [M+H]$^+$ (calcd for C$_{36}$H$_{41}$O$_9$, 617.2751); CD [nm (Δε (2.7 mg/50 ml MeOH): 363 (+2.2), 321 (−0.3), 296 (+1.3), 271 (−9.2), 250 (+10.0), 241 (+6.3), 216 (−2.5).

Mib-8 was further subjected to X-ray crystallography analysis, in which a suitable colorless crystal (0.25×0.20×0.15 mm$^3$), grown by slow evaporation of MeOH solution, was mounted on a Nonius CCD diffractometer equipped with Cu radiation (λ=1.54178 Å). Crystal data: C$_{38}$H$_{48}$O$_{11}$, Mr=680.76 g/mol, orthorhombic. Cell parameter: a=7.72090(10), b=15.8528(3), c=28.9225(5) Å, V=3540.05 (10) Å$^3$, space group P2$_1$2$_1$2$_1$ (Z=4), D$_{calc}$=1.277 mg/m$^3$, F(000)=1456. A total of 12264 reflections were collected (6451 unique, $R_{int}$=0.0232) in the range 3.06°<θ<67.96°. The structure was solved using direct methods and refined by Full-matrix least-squares on $F^2$ values. The final indices were $R_1$=0.0515, $wR_2$=0.1444 with goodness-of-fit=0.989.

1.2.5 Mib-9

UV (MeOH) $\lambda_{max}$ (log ε) 250 (3.70), 277 sh. (3.58) nm; IR (KBr) $\nu_{max}$ 3469, 1705, 1624, 1375, 1085 cm$^{-1}$; $[\alpha]^{26}_D$ −51.6° (c 0.35, MeOH); $^1$H NMR (CDCl$_3$, 600 MHz); $^{13}$C NMR (CDCl$_3$, 150 MHz) see Tables 1 and 2; ESIMS m/z 599 [M−H]$^-$; HRESIMS m/z 601.2804 [M+H]$^+$ (calcd for C$_{36}$H$_{41}$O$_8$, 601.2801); CD [nm (Δε (2.9 mg/50 ml MeOH): 308 (+0), 291 (+1.4), 276 (+0.3), 261 (+2.5), 244 (−2.4), 236 (−1.8), 223 (−3.5), 212 (−3.7).

1.2.6 Mib-10

UV (MeOH) $\lambda_{max}$ (log ε) 240 sh. (4.13), 278 (4.04) nm; IR (KBr) $\nu_{max}$ 3433, 1709, 1668, 1645, 1464, 1381, 1322, 1209, 1175 cm$^{-1}$; $[\alpha]^{26}_D$ +234.7° (c 0.42, MeOH); $^1$H NMR (CDCl$_3$, 600 MHz); $^{13}$C NMR (CDCl$_3$, 150 MHz) see Tables 1 and 2; ESIMS m/z 599 [M−H]$^-$; HRESIMS m/z 601.2794 [M+H]$^+$ (calcd for C$_{36}$H$_{41}$O$_8$, 601.2801); CD [nm (Δε (2.9 mg/50 ml MeOH): 340 (+2.8), 316 (+0.4), 306 (+0.7), 265 (−7.5), 244 (+9.8), 229 (+6.4), 221 (+7.9), 207 (+2.3).

TABLE 1

$^1$H NMR Data (600 MHz) for Mib-5 to Mib-10 (δ in ppm and J in Hz)

| positions | Mib-5[a] | Mib-6[a] | Mib-7[b] | Mib-8[b] | Mib-9[a] | Mib-10[a] |
|---|---|---|---|---|---|---|
| 1 | 0.87/1.38 | 0.90/1.38 | 0.95/1.41 | 0.93/1.74 | 0.91/1.44 | 0.94/1.62 |
| 2 | 1.46/1.55 | 1.47/1.57 | 1.45/1.60 | 1.44/1.55 | 1.53/1.58 | 1.37/1.53 |
| 3a | 1.12 td (13.2, 3.0) | 1.15 td (13.2, 3.0) | 1.17 td (14.4, 3.0) | 1.17 td (13.2, 3.0) | 1.14 td (13.8, 3.0) | 1.15 td (12.5, 3.0) |
| 3b | 1.38 d (13.8) | 1.38 m | 1.41 m | 1.44 m | 1.39 d (15.0) | 1.37 m |
| 6 | 5.43 s | 5.44 s | 5.46 s | 5.54 d (6.0) | 5.42 s | 5.51 s |
| 7 | 2.19 m | 2.19 m | 2.17 m | 2.15 m/2.25 m | 2.12 m/2.20 m | 2.25 m |
| 8 | 2.40 m | 2.40 m | 2.42 m | 2.67 m | 2.41 m | 2.73 m |
| 10 | 2.40 m | 2.40 m | 2.42 m | 2.39 d (12.6) | 2.41 m | 2.35 d (12.0) |
| 11a | 1.30 d (12.6) | 1.24 d (12.6) | 1.26 d (13.2) | 1.31 d (12.6) | 1.32 d (12.6) | 1.37 m |
| 11b | 1.89 t (13.8) | 1.90 t (13.8) | 2.01 m | 1.88 t (12.6) | 1.88 t (12.6) | 1.85 t (13.5) |
| 12 | 3.22 d (10.2) | 3.30 d (10.2) | 3.32[b] | 3.42 d (12.6) | 3.29 d (10.8) | 3.43 d (11.5) |
| 14 | 5.33 d (6.0) | 5.31 d (6.0) | 5.35 d (6.0) | 5.44 d (5.4) | 5.34 d (4.8) | 5.41 d (6.0) |
| 15a | 2.05 m | 2.02 m | 2.07 m | 2.15 m | 2.05 m | 2.13 d (13.5) |
| 15b | 2.72-2.77 | 2.73 | 2.75-2.80 | 2.85-2.90 | 2.70-2.75 | 2.88-2.94 |
| 16 | 1.95 s | 1.93 s | 1.92 s | 1.94 s | 1.95 s | 1.98 s |
| 18 | 1.01 s | 1.03 s | 1.03 s | 1.05 s | 1.02 s | 1.04 s |
| 19 | 1.01 s | 1.02 s | 1.06 s | 0.98 s | 1.01 s | 0.95 s |
| 20 | 0.86 s | 0.88 s | 0.91 s | 0.85 s | 0.85 s | 0.85 s |
| 3' | 6.33 s | 6.25 s | 6.17 s | 6.20 s | 6.33 s | 6.39 s |
| 5' | 8.01 d (9.0) |  |  |  | 8.01 d (9.0) | 7.75 d (7.5) |
| 6' | 6.94 dd (9.0, 2.4) | 6.32 d (2.0) | 6.19 d (1.8) | 6.17 d (1.8) | 6.92 d (9.0) | 6.73 m |
| 8' | 6.80 d (2.4) | 6.36 d (2.0) | 6.29 d (1.8) | 6.22 d (1.8) | 6.95 s | 6.73 m |
| 7'-OCH$_3$ | 3.88 s | 3.83 s |  |  |  |  |
| 3" | 5.78 s | 5.79 s | 5.96 s | 5.96 s | 5.80 s | 5.80 s |
| 6" | 3.86 m | 3.81 m | 3.80 dd (10.8, 5.4) | 4.01 dd (11.4, 5.4) | 3.91 m | 4.06 dd (10.0, 5.0) |
| 4'-OCH$_3$ | 3.71 s | 3.72 s | 3.75 s | 3.75 s | 3.71 s | 3.71 s |

[a]measured in CDCl$_3$;
[b]measured in methanol-d$_4$.

TABLE 2

$^{13}$C NMR Data (150 MHz) for Mib-5~Mib-10 (δ in ppm)

| position | Mib-5[a] δ$_C$, type | Mib-6[a] δ$_C$, type | Mib-7[b] δ$_C$, type | Mib-8[b] δ$_C$, type | Mib-9[a] δ$_C$, type | Mib-10[a] δ$_C$, type |
|---|---|---|---|---|---|---|
| 1 | 27.0, CH$_2$ | 26.9, CH$_2$ | 28.0, CH$_2$ | 28.8, CH$_2$ | 27.2, CH$_2$ | 27.4, CH$_2$ |
| 2 | 22.0, CH$_2$ | 22.0, CH$_2$ | 23.2, CH$_2$ | 22.9, CH$_2$ | 22.0, CH$_2$ | 21.8, CH$_2$ |
| 3 | 40.6, CH$_2$ | 40.6, CH$_2$ | 42.0, CH$_2$ | 42.0, CH$_2$ | 40.6, CH$_2$ | 40.6, CH$_2$ |
| 4 | 36.3, C | 36.3, C | 37.2, C | 37.3, C | 36.3, C | 36.3, C |
| 5 | 145.9, C | 145.9, C | 147.1, C | 147.9, C | 145.9, C | 146.3, C |
| 6 | 114.7, CH | 114.7, CH | 116.4, CH | 116.3, CH | 114.5, CH | 115.1, CH |
| 7 | 27.1, CH$_2$ | 27.2, CH$_2$ | 28.4, CH$_2$ | 28.2, CH$_2$ | 26.9, CH$_2$ | 27.1, CH$_2$ |
| 8 | 45.5, CH | 45.5, CH | 46.8, CH | 47.5, CH | 45.9, CH | 45.5, CH |
| 9 | 36.7, C | 36.4, C | 37.7, C | 38.7, C | 36.8, C | 37.6, C |
| 10 | 40.2, CH | 40.0, CH | 41.6, CH | 41.6, CH | 40.1, CH | 40.0, CH |
| 11 | 37.4, CH$_2$ | 37.1, CH$_2$ | 38.4, CH$_2$ | 37.2, CH$_2$ | 37.7, CH$_2$ | 35.5, CH$_2$ |
| 12 | 40.2, CH | 40.3, CH | 41.7, CH | 42.3, CH | 40.6, CH | 40.9, CH |
| 13 | 141.0, C | 140.9, C | 141.5, C | 143.4, C | 140.5, C | 142.7, C |
| 14 | 120.9, CH | 121.0, CH | 122.7, CH | 121.5, CH | 121.1, CH | 119.5, CH |
| 15 | 26.0, CH$_2$ | 26.0, CH$_2$ | 26.8, CH$_2$ | 26.7, CH$_2$ | 26.0, CH$_2$ | 25.8, CH$_2$ |
| 16 | 25.6, CH$_3$ | 25.6, CH$_3$ | 26.1, CH$_3$ | 26.7, CH$_3$ | 25.8, CH$_3$ | 26.2, CH$_3$ |
| 17 | 177.3, C | 178.8, C | 178.7, C | 178.4, C | 178.8, C | 178.5, C |
| 18 | 29.5, CH$_3$ | 29.5, CH$_3$ | 30.0, CH$_3$ | 30.1, CH$_3$ | 29.5, CH$_3$ | 29.5, CH$_3$ |
| 19 | 28.5, CH$_3$ | 28.5, CH$_3$ | 29.0, CH$_3$ | 29.2, CH$_3$ | 28.5, CH$_3$ | 28.6, CH$_3$ |
| 20 | 18.5, CH$_3$ | 18.7, CH$_3$ | 19.4, CH$_3$ | 18.6, CH$_3$ | 18.7, CH$_3$ | 18.1, CH$_3$ |
| 2' | 164.9, C | 165.9, C | 167.9, C | 167.7, C | 165.1, C | 165.4, C |
| 3' | 111.0, CH | 109.4, CH | 109.8, CH | 109.9, CH | 110.5, CH | 110.1, CH |
| 4' | 176.9, C | 181.5, C | 182.8, C | 183.2, C | 177.2, C | 177.5, C |
| 5' | 127.0, CH | 161.9, C | 163.2, C | 163.1, C | 127.5, CH | 127.1, CH |
| 6' | 115.5, CH | 99.0, CH | 100.7, CH | 100.9, CH | 115.7, CH | 116.0, CH |
| 7' | 164.4, C | 165.9, C | 166.7, C | 166.9, C | 161.9, C | 162.6, C |
| 8' | 100.0, CH | 92.3, CH | 95.1, CH | 95.1, CH | 102.9, CH | 102.7, CH |
| 9' | 157.8, C | 157.5, C | 159.1, C | 159.2, C | 157.7, C | 157.8, C |
| 10' | 117.3, C | 105.3, C | 105.1, C | 105.1, C | 116.9, C | 116.1, C |
| 7'-OCH$_3$ | 56.5, CH$_3$ | 55.9, CH$_3$ | | | | |
| 1''' | 62.8, C | 62.8, C | 64.1, C | 64.5, C | 62.8, C | 63.3, C |
| 2'' | 192.6, C | 192.2, C | 194.1, CH | 194.4, C | 192.7, C | 192.8, C |
| 3'' | 111.0, CH | 111.1, CH | 112.1, CH | 112.2, CH | 111.2, CH | 111.4, CH |
| 4'' | 160.3, C | 160.4, C | 162.4, C | 162.6, C | 160.2, C | 160.6, C |
| 5'' | 193.7, C | 193.5, C | 195.2, C | 195.0, C | 194.1, C | 194.0, C |
| 6'' | 43.1, CH | 43.0, CH | 44.6, CH | 44.1, CH | 43.0, CH | 42.8, CH |
| 4''-OCH$_3$ | 56.0, CH$_3$ | 56.6, CH$_3$ | 57.4, CH$_3$ | 57.4, CH$_3$ | 56.6, CH$_3$ | 56.6, CH$_3$ |

[a]measured in CDCl$_3$;
[b]measured in methanol-d4.

1.3 Effects of the Present Compounds on Farnesyl Transferase Activity

In this example, compounds of formula (1a) and (1b) were tested for their respective activities toward farnesyl transferase, in which FTase Inhibitor II was employed as a positive control, and results are summarized in Table 2.

As indicated in Table 3, Mib-5, 6, 7, and 8 appeared to be more potent than Mib-9 and Mib-10, with respective half maximal inhibitory concentrations (IC$_{50}$) being less than 10 μM, while the IC$_{50}$ values for Mib-9 and Mib-10 were respectively about 47 and 28 μM. Accordingly, only Mib-5, Mib-6, Mib-7, Mib-8, and Mib-10 were employed for the subsequent analysis in examples 1.2 and 1.3.

TABLE 3

IC$_{50}$ values of the present compounds on farnesyl transferase

| Compound | IC$_{50}$ (μM) |
|---|---|
| Mib-5 | 7.51 ± 0.10 |
| Mib-6 | 4.97 ± 0.00 |
| Mib-7 | 8.46 ± 0.08 |
| Mib-8 | 5.05 ± 0.06 |
| Mib-9 | 46.97 ± 1.48 |
| Mib-10 | 27.85 ± 1.45 |
| FTase Inhibitor II[b] | 0.13 ± 0.03 |

[a] The values represent as mean ± SD of three independent experiments.
[b]Reported IC$_{50}$ value of FTase inhibitor II is 50-75 nM.

1.4 Effects of the Present Compounds on Viability, Morphology, Polarization and Cellular Functions of Macrophages In this example, effects of Mib-5, Mib-6, Mib-7, Mib-8, and Mib-10 on cellular functions of macrophages, including morphology changes, cell viability, differentiation, and expression of various types of cell markers, were investigated by use of methods described in the "Material and Methods" section. Results are illustrated in FIGS. 1 to 5, and Tables 3 to 6.

Referring to FIG. 1, in which representative photographs are presented. For cells treated with Mib-8 or Mib-10, about 20% of them exhibited adhesive morphology (FIG. 1, panel A), while cells treated with Mib-5, Mib-6, or Mib-7 became rounded up, and were less adhesive on the supporting substrate (FIG. 1, panel B). The morphology of cells were further analyzed by Liu's staining; and the data indicated that, compared with that of the control cells, the morphology of cells was not significantly affected by the treatment of any of the compound of example 1.1 (i.e., Mib-5, Mib-6, Mib-7, Mib-8, or Mib-10) (FIG. 1, panel C).

Figure 2:
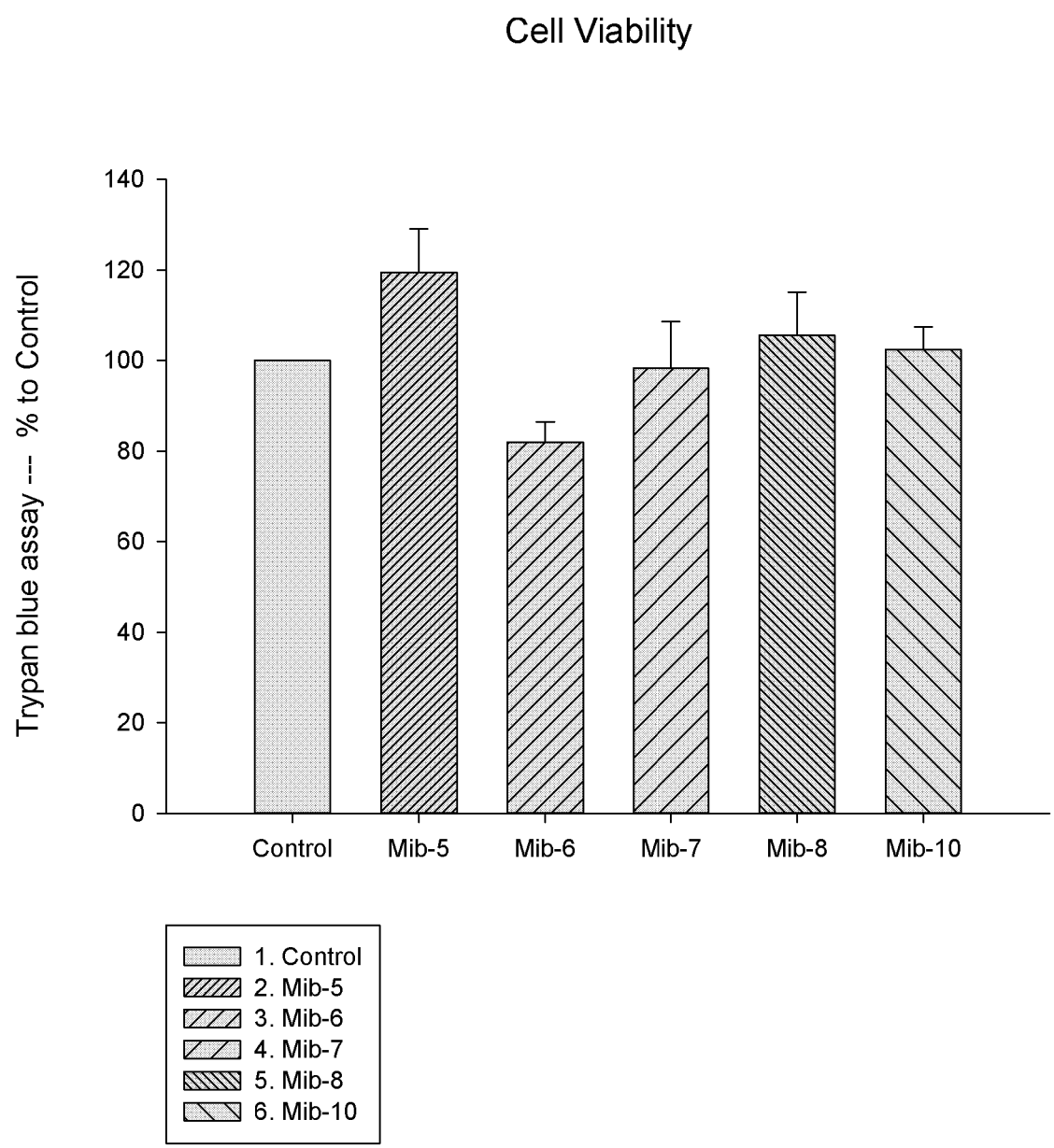
FIG. 2 is a histogram that depicts the cell viability of macrophages respectively treated with specified compounds according to another example of the present disclosure.

Trypan blue analysis further confirmed that, except for Mib-6, which appeared to exhibit slight toxicity toward macrophages, Mib-5, Mib-7, Mib-8, and Mib-10 did not adversely affect cell viability, respectively (FIG. 2). The data indicated that among the compounds of formula (1a) and (1b), Mib-5, Mib-7, Mib-8, and Mib-10 may respectively inhibit farnesyl transferase without affecting cell viability of macrophages.

As to the effects of the present compounds on the differentiation of macrophages, results are summarized in Table 4. Compared with the control group (i.e., cells without any treatment), treatment with Mib-7 or Mib-10 resulted in a decrease in the M1 population of macrophages, while the M2 population increased about 40%. As to the effect of Mib-5 or Mib-6, each compound resulted in a significant reduction in M1, and a slight decrease in M2 population. Mib-8 had no effect on M2 population, yet it also resulted in about 20% reduction in the M1 population.

TABLE 4

Cell viability of M1 and M2 macrophages

| Compound | M1 | M2 |
| --- | --- | --- |
| Control | 100% | 100% |
| Mib-5 | 63.5% | 86.4% |
| Mib-6 | 57.2% | 90.6% |
| Mib-7 | 82.5% | 136.4% |
| Mib-8 | 79.4% | 100% |
| Mib-10 | 82.5% | 145.5% |

Figure 3:
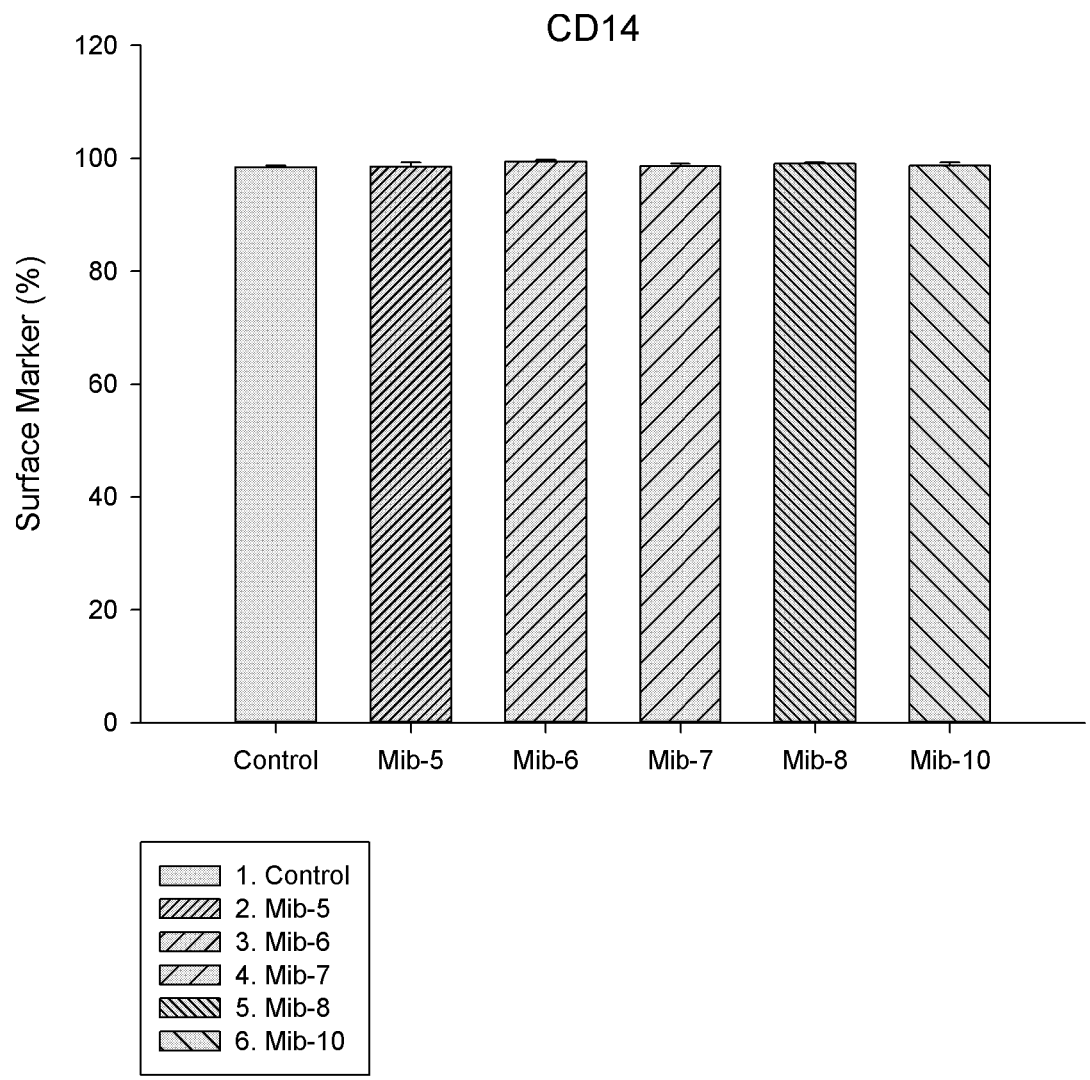
FIG. 3 is a histogram that depicts CD14 expression of the macrophages respectively treated with specified compounds according to one example of the present disclosure.
Figure 4:
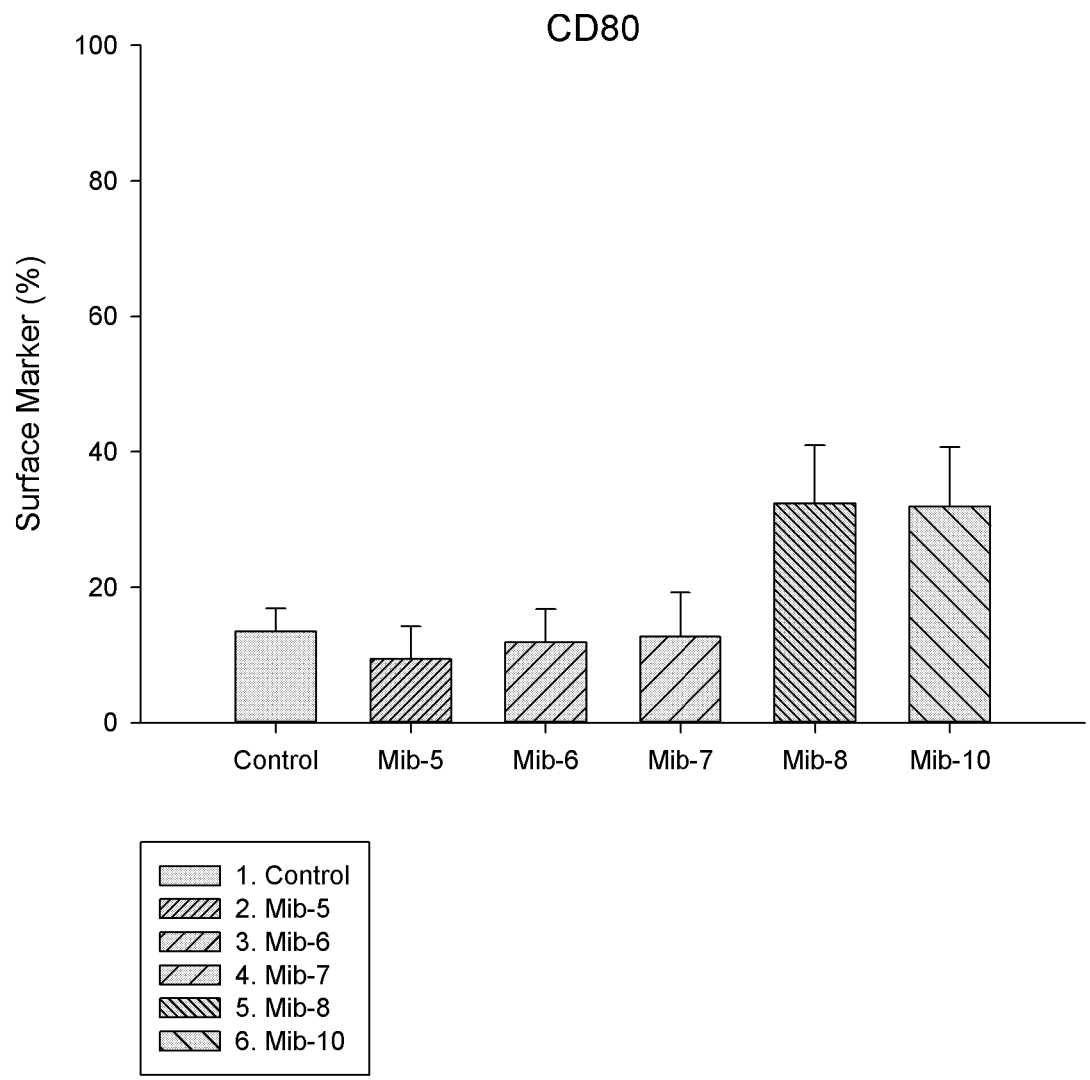
FIG. 4 is a histogram that depicts CD80 expression of the macrophages respectively treated with specified compounds according to another example of the present disclosure.
Figure 5:
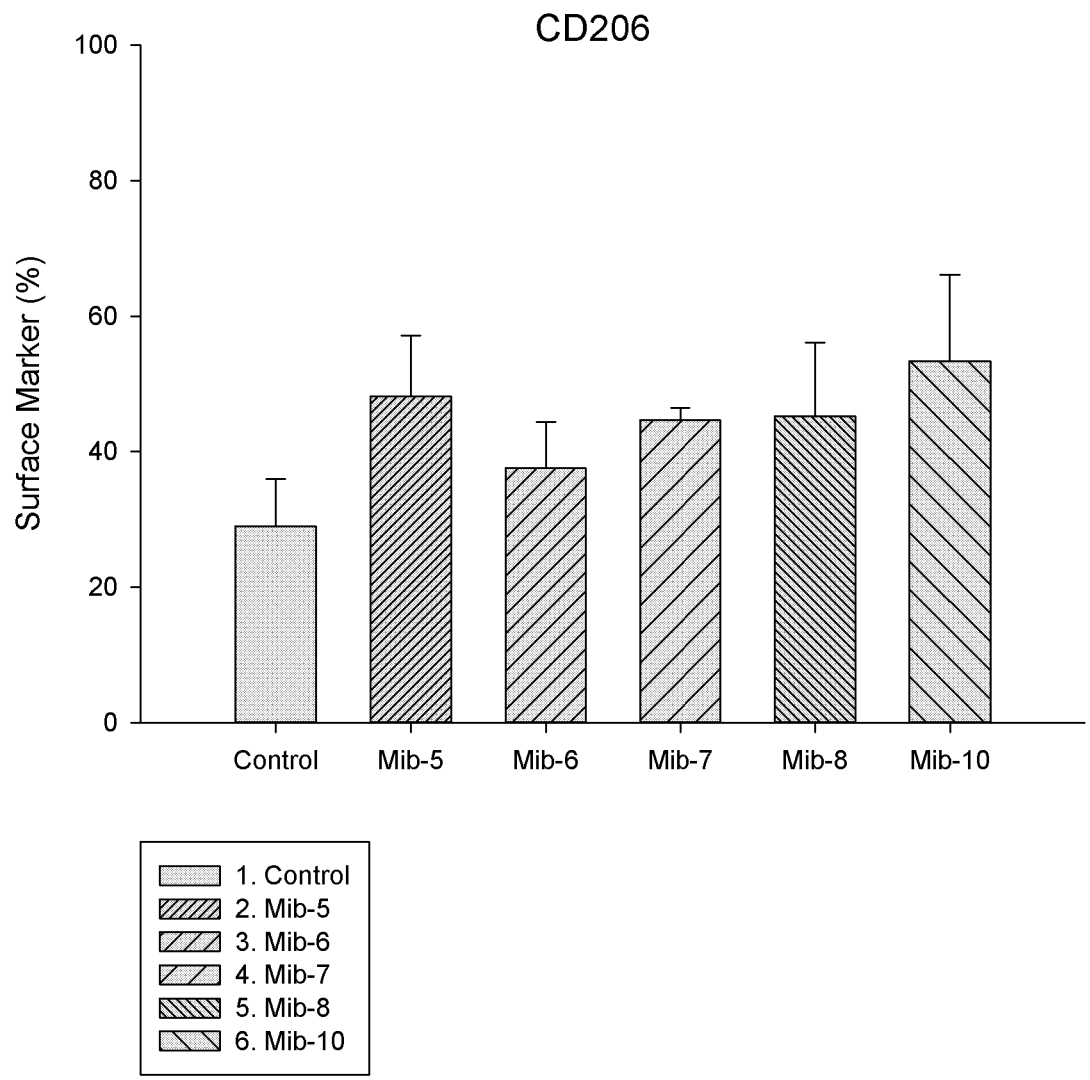
FIG. 5 is a histogram that depicts CD206 expression of the macrophages respectively treated with specified compounds according to still another example of the present disclosure.

The effects of the present compounds on the expression of cell markers including CD14, CD80 and CD206 are respectively illustrated in FIGS. 3 to 5, and Tables 5 to 7.

It is noted that, in general, the total expressed level of CD14 was not affected by the treatment of any of Mib-5, Mib-6, Mib-7, Mib-8 or Mib-10 (FIG. 3). Further, M1 population remained relatively unchanged, while significant decrease in M2 population was found (Table 5) after cells were treated with the present compounds (i.e., Mib-5, Mib-6, Mib-7, Mib-8 or Mib-10). As to CD80, the total level of CD80 was significantly reduced by the treatment of Mib-5, Mib-6, or Mib-7, and increased by the treatment of Mib-8 or Mib-10 (about 2-folds increase as compared with the control) (FIG. 3). Further, a reduction in M1 population was found when cells were treated with Mib-5, Mib-6, Mib-7, or Mib-8; whereas an increase in M2 population was observed if treated with Mib-5, Mib-7, Mib-8 or Mib-10 (Table 6). Regarding CD206, an increase in the level of CD206 was found by the treatment of any of Mib-5, Mib-6, Mib-7, Mib-8 or Mib-10 (FIG. 5), while a significant decrease in M1 was found when treated with Mib-5, Mib-6, Mib-7, or Mib-8, and an increase in M2 was found when treated with Mib-5, Mib-6, or Mib-7 (Table 7).

TABLE 5

CD14 expression on M1 and M2 macrophages

| Compound | M1 | M2 |
| --- | --- | --- |
| Control | 99.83% | 55.66% |
| Mib-5 | 97.03% | 80.33% |
| Mib-6 | 86.43% | 91.25% |
| Mib-7 | 98.66% | 89.76% |
| Mib-8 | 99.73% | 62.34% |
| Mib-10 | 99.10% | 57.93% |

TABLE 6

CD80 expression on M1 and M2 macrophages

| Compound | M1 | M2 |
| --- | --- | --- |
| Control | 71.34% | 47.64% |
| Mib-5 | 11.94% | 53.03% |
| Mib-6 | 6.59% | 41.4% |
| Mib-7 | 23.04% | 49.58% |
| Mib-8 | 60.16% | 56.66% |
| Mib-10 | 84.46% | 59.89% |

TABLE 7

CD206 expression on M1 and M2 macrophages

| Compound | M1 | M2 |
| --- | --- | --- |
| Control | 14.27% | 74.49% |
| Mib-5 | 5.41% | 78.77% |
| Mib-6 | 4.52% | 77.78% |
| Mib-7 | 4.9% | 88.88% |
| Mib-8 | 11.98% | 51.05% |
| Mib-10 | 15.17% | 68.80% |

Figure 6:
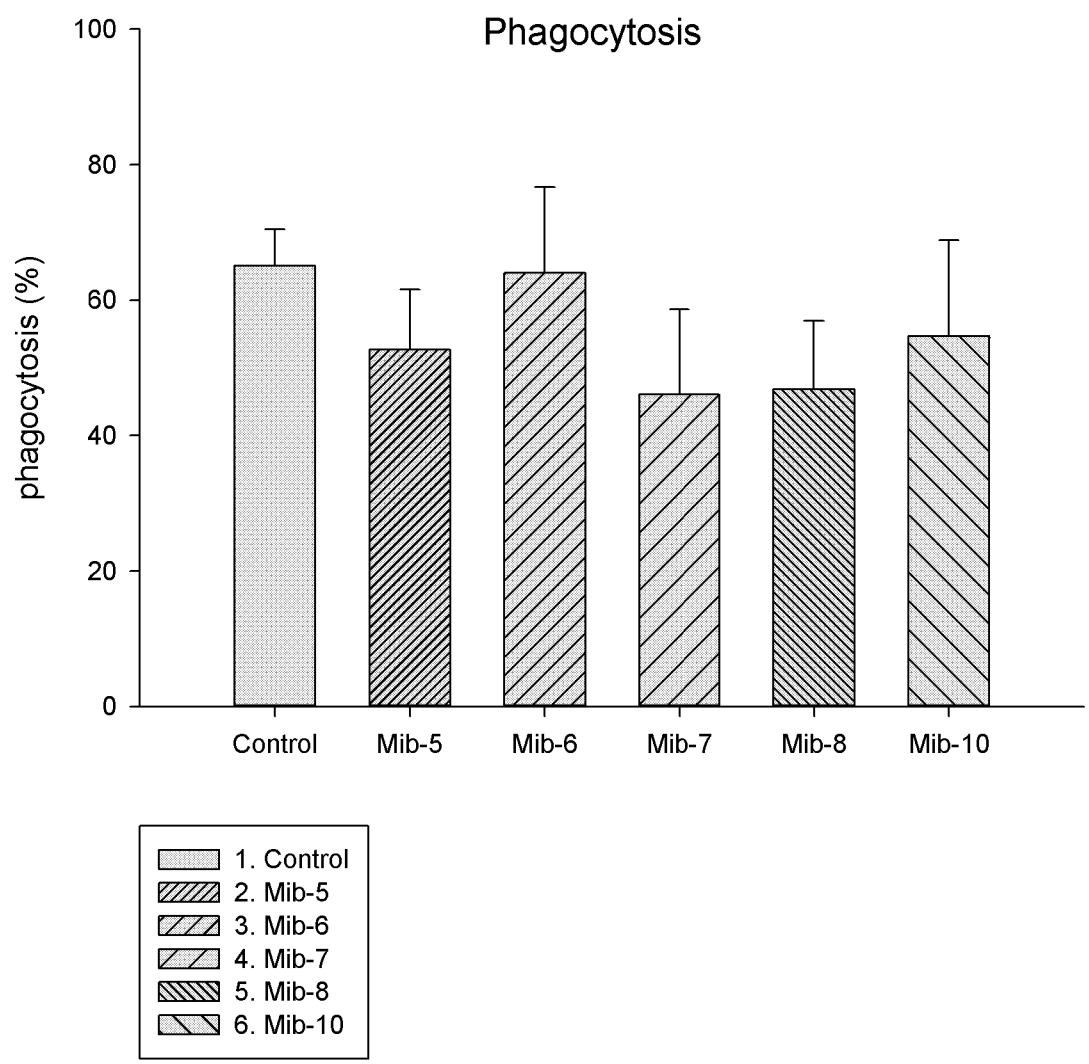
FIG. 6 is a histogram that depicts the percentage of phagocytosis of macrophages respectively treated with specified compounds according to one example of the present disclosure.

Effects of the present compounds on phagocytic activities of the M1 and/or M2 populations were depicted in FIG. 6, in which the phagocytic activity was found to be reduced by the treatment of Mib-5, Mib-7, Mib-8 and Mib-10, but not by Mib-6, when compared with that of the control.

Taken together, data in the present example indicated that each of the present identified farnesyl transferase inhibitors, including Mib-5, Mib-6, Mib-7, Mib-8, and Mib-10, possess no significant cytotoxicity, yet it may tilt the balance between the M1/M2 populations toward the accumulation of M2 population. Accordingly, the present compounds can be used as a lead compound for the development of an anti-inflammatory agent for the treatment of an immune disease caused by excessive immune response.

1.5 Effects of the Present Compounds on Viability, Morphology, Differentiation and Maturation of Dendritic Cell In this example, the effects of the present compounds on dendritic cells were investigated. Briefly, the dendritic cells were respectively treated with 10 μM of Mib-5, Mib-6, Mib-7, Mib-8, or Mib-10. Seven days later, the cells were harvested and subjected to analysis of morphology observation, cell viability, and/or cell marker expression.

Figure 7:
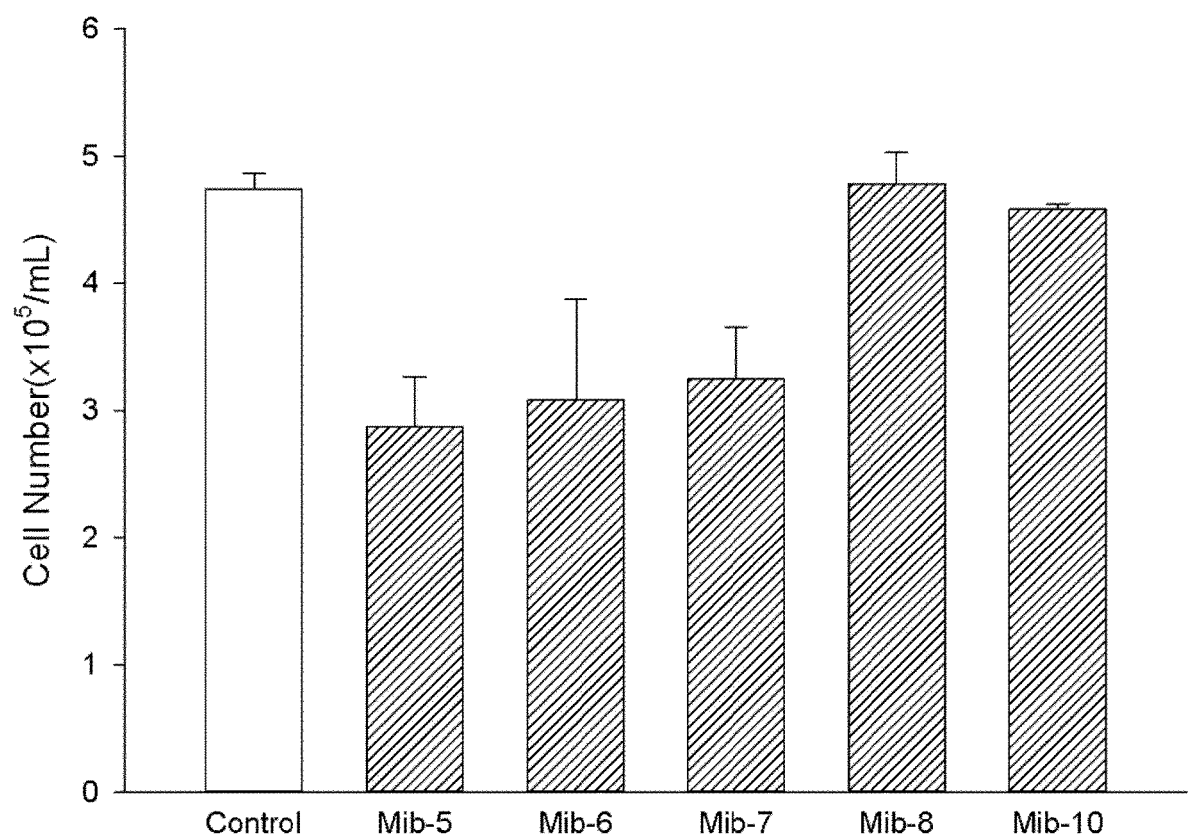
FIG. 7 is a histogram that depicts the cell number of dendritic cells respectively treated with specified compounds according to one example of the present disclosure.

According to the trypan blue exclusion analysis, the respective levels of viable dendritic cells were reduced by the treatment of Mib-5, Mib-6, or Mib-7, while the cell viability remained relatively unchanged by the treatment of Mib-8 and Mib-10, respectively (FIG. 7).

Figure 8:
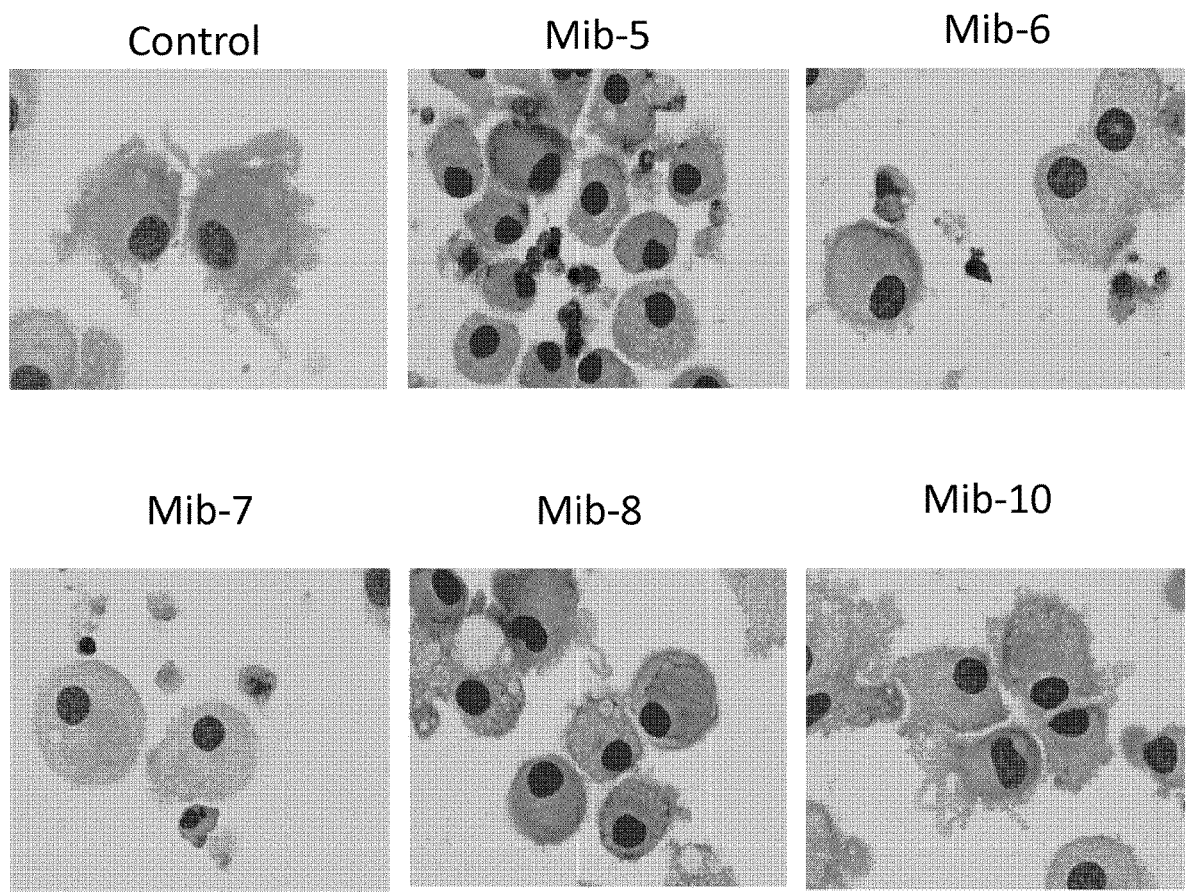
FIG. 8 are the photographs illustrating the morphology of dendritic cells treated with specified compounds according to one example of the present disclosure.

The cell morphology was analyzed by Liu's staining. The data suggested that compared with that of the control group, treatment of Mib-5, Mib-6, or Mib-7 resulted in cell death reflected in morphology changes, and less dendritic process. By contrast, treatment with Mib-8 or Mib-10 did not cause any significant changes in cell morphology (FIG. 8).

Figure 9:
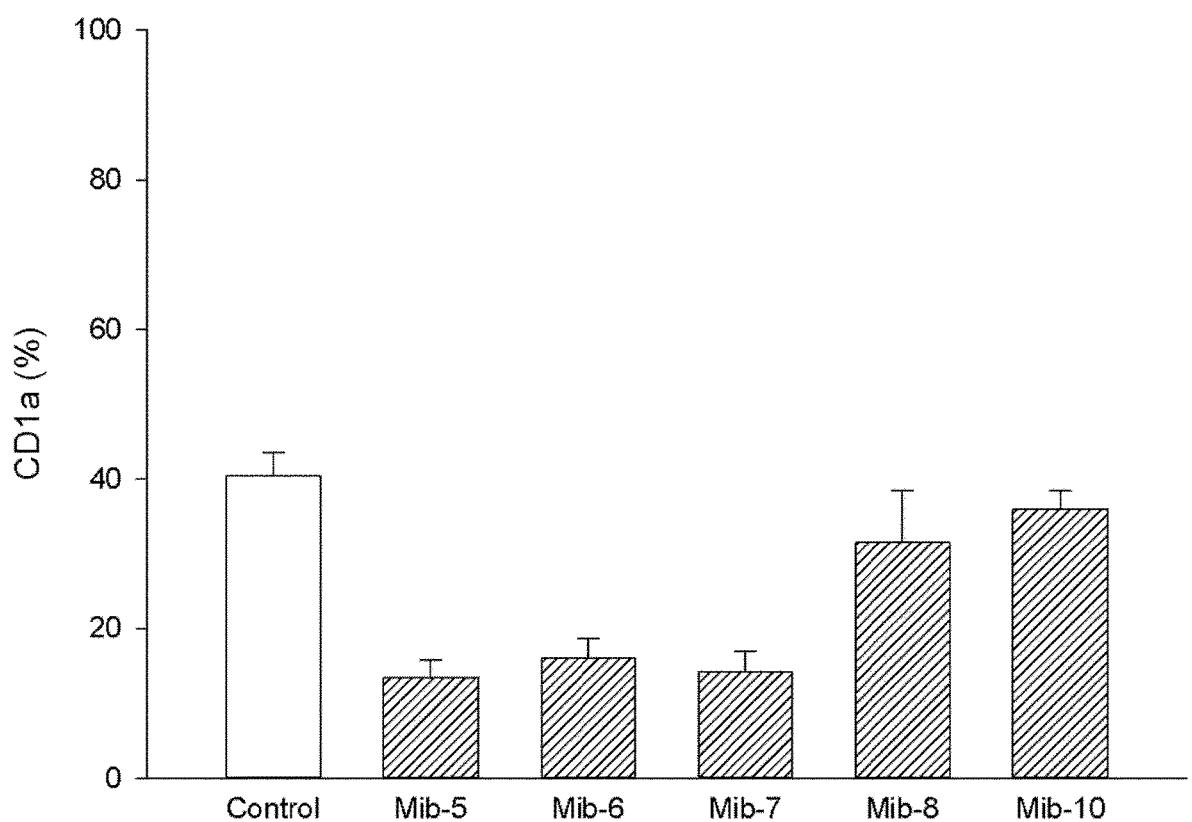
FIG. 9 is a histogram that depicts CD1a expression of dendritic cells respectively treated with specified compounds according to another example of the present disclosure.
Figure 10:
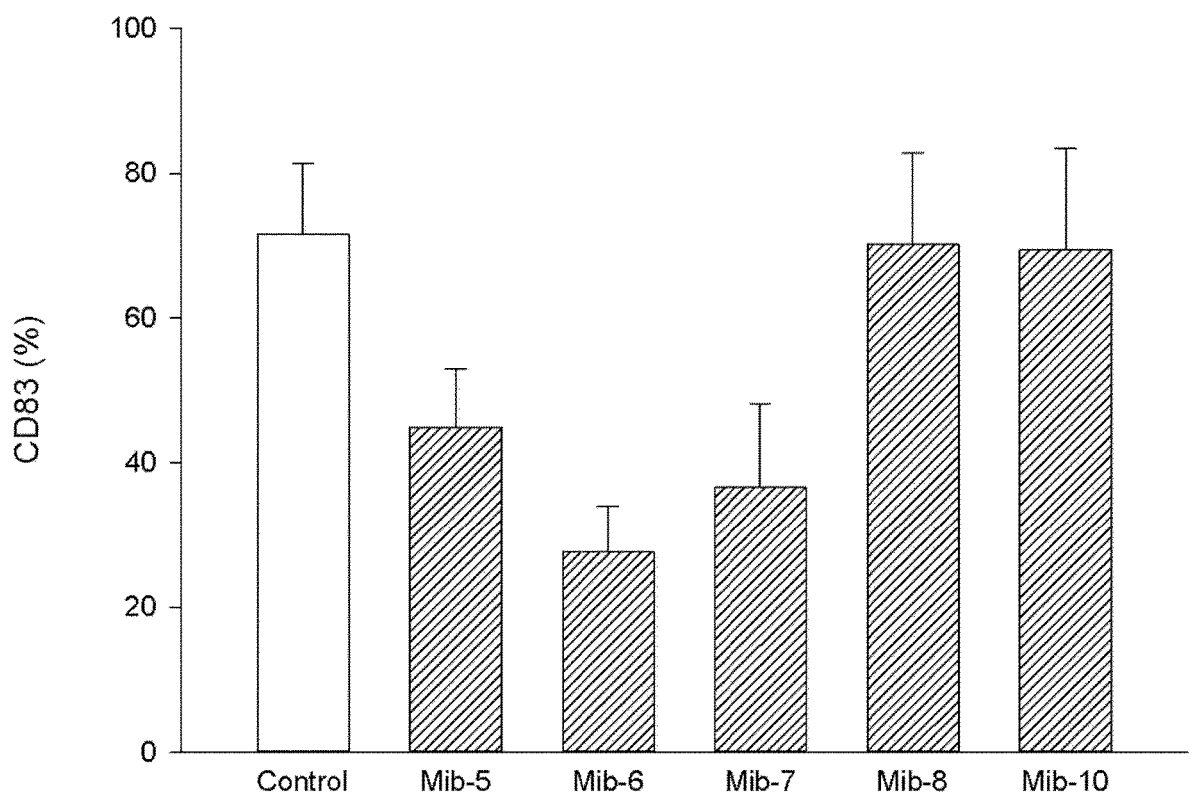
FIG. 10 is a histogram that depicts CD83 expression of dendritic cells respectively treated with specified compounds according to one example of the present disclosure.
Figure 11:
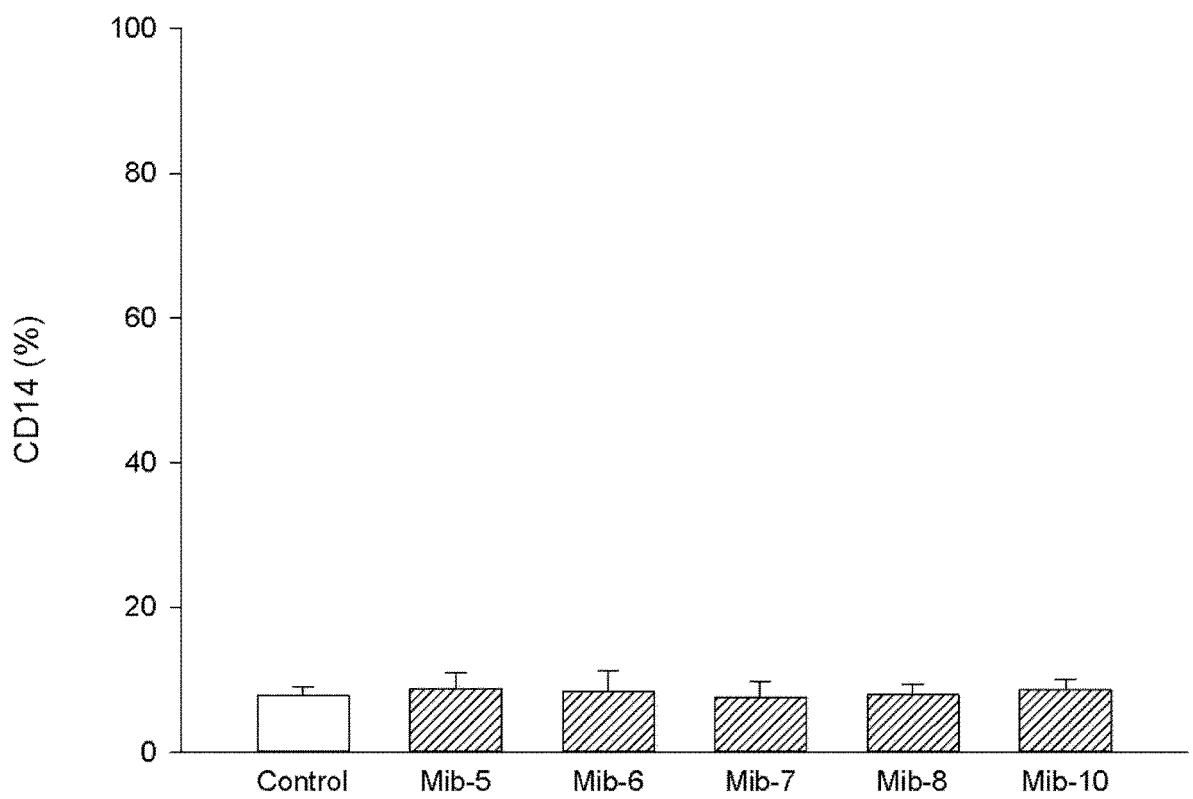
FIG. 11 is a histogram that depicts CD14 expression of dendritic cells respectively treated with specified compounds according to one example of the present disclosure.
Figure 12:
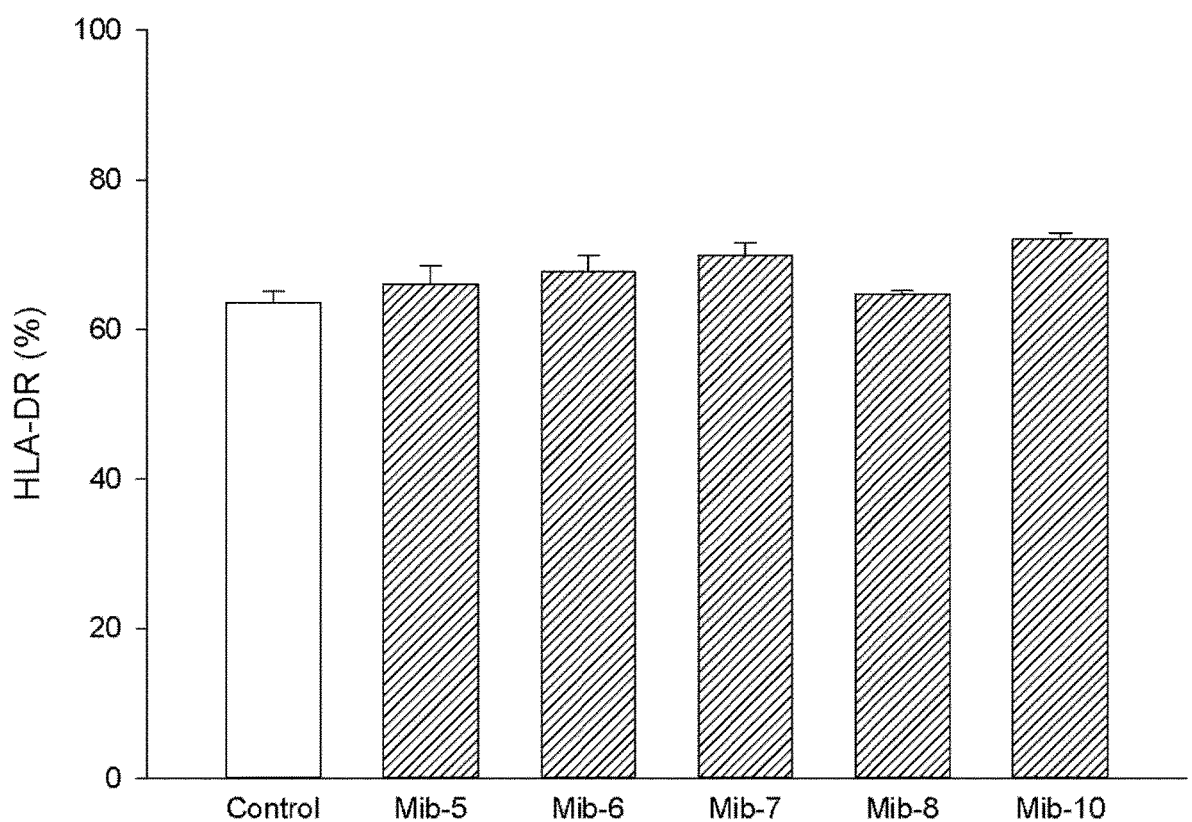
FIG. 12 is a histogram that depicts HLA-DR expression of dendritic cells respectively treated with specified compounds according to one example of the present disclosure.

The expression of CD1a, CD14, CD83 or HLA-DR on dendritic cells was analyzed by flow cytometer. The expression of CD1a, the differentiation marker of dendritic cells, was inhibited by Mib-5, Mib-6 or Mib-7, but not by Mib-8 or Mib-10 (FIG. 9). The expression of CD83, the maturation marker of dendritic cells, was inhibited by Mib-5, Mib-6 or Mib-7, but not affected by Mib-8 or Mib-10 (FIG. 10). Expression of the monocyte/macrophage marker (CD14) for evaluation of de-differentiation (FIG. 11) and the MHC class II molecule HLA-DR (FIG. 12) was not affected by any of the present Mib compounds.

The collective data herein indicated that Mib-5, Mib-6, and Mib-7 may respectively suppress the viability, differentiation and maturation of dendritic cells.

Figure 13:
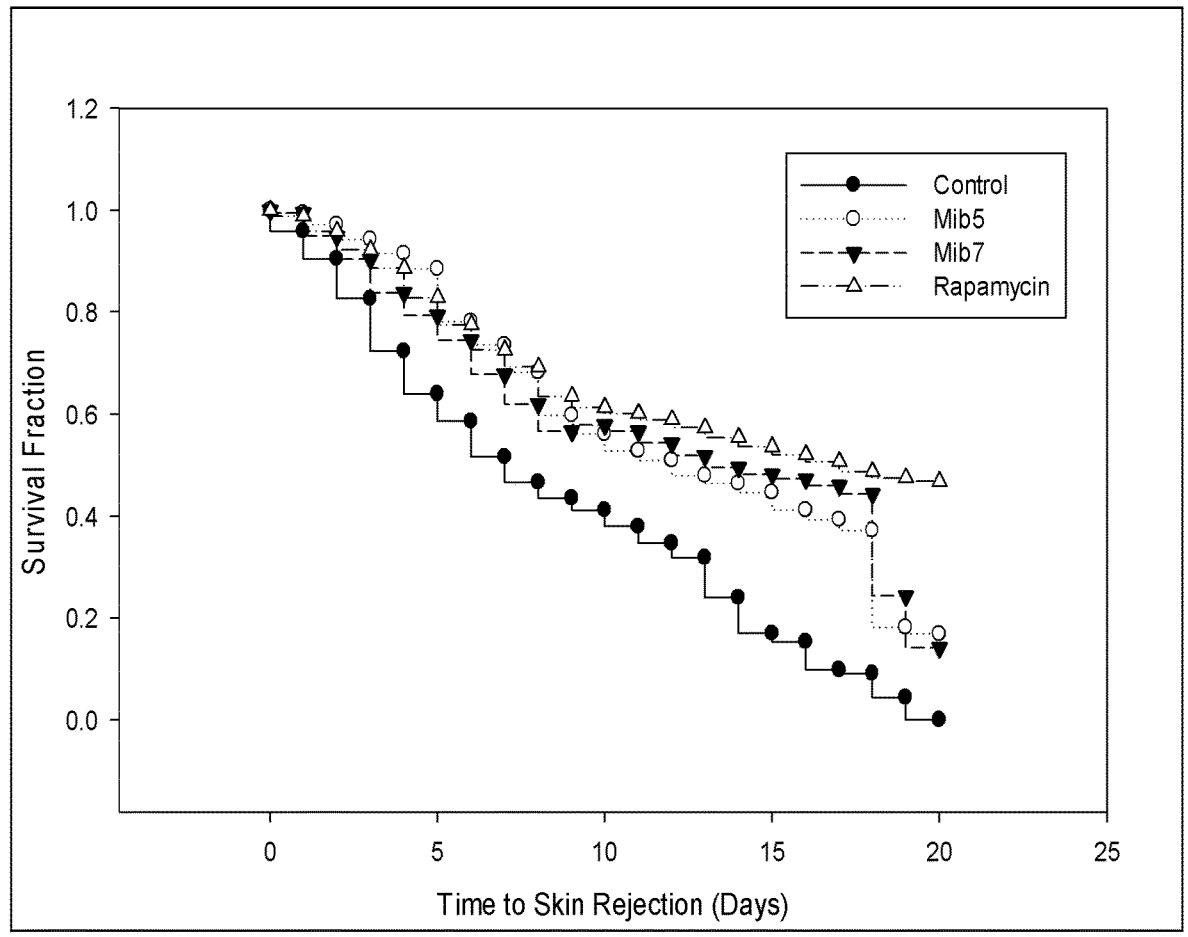
FIG. 13 is a survival curve that depicts the survival of skin allografts in recipient mice respectively treated with specified compounds according to another example of the present disclosure.

Example 2 In Vivo Effect of Mib-5 and Mib-7 by Experimental Animal Model of Skin Transplantation Rejection The skin allo-transplantation model, by using C57BL/6 (H-2$^b$) mice as donors and BALB/c(H-2$^d$) mice as recipients, was used to examine the effect of Mib-5 and Mib-7 on allograft survival, in which rapamycin served as a positive control. As the data of FIG. 13, the mean survival of skin allograft in recipient mice was significantly prolonged by treatment with Mib-5 or Mib-7.

In conclusion, the present disclosure provides six novel compounds (i.e., Mib-5, Mib-6, Mib-7, Mib-8, Mib-9, and Mib-10), in which five of them (i.e., Mib-5, Mib-6, Mib-7, Mib-8, and Mib-10) were capable of inhibiting the activity of farnesyl transferase, without generating any cytotoxicity. Further, the present disclosure also demonstrates that the five compounds that inhibit farnesyl transferase (i.e., Mib-5, Mib-6, Mib-7, Mib-8, and Mib-10) may modulate polarization and cellular functions of macrophages as well as the differentiation and maturation of dendritic cells. Accordingly, the present compounds are potential candidates for the development of lead compounds for manufacturing a medicament for treating disease and/or disorders associated with the activation of farnesyl transferase, such as immune diseases.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating a subject having or suspected of having a disease or a disorder associated with the activation of farnesyl transferase, comprising administering to the subject a therapeutically effective amount of the compound of formula (1),

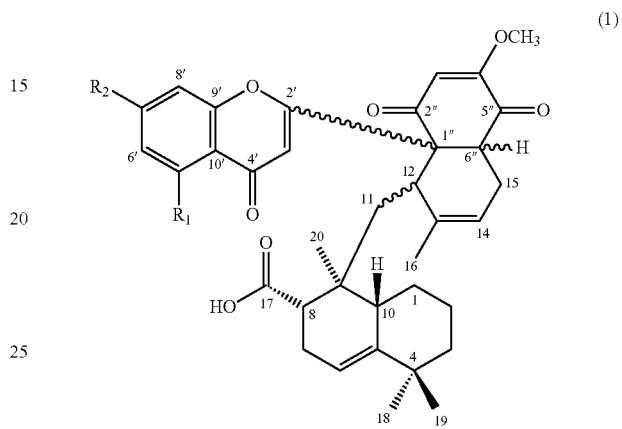

wherein, $R_1$ is H or hydroxyl; and $R_2$ is hydroxyl or methoxy; and the disease or disorder associated with the activation of farnesyl transferase is skin transplantation rejection.

2. The method of claim 1, wherein the subject is a human.

3. The method of claim 1, wherein the compound of formula (1) is administered to the subject in the amount of about 0.08-10.0 mg/Kg.

* * * * *